(12) United States Patent
Goto et al.

(10) Patent No.: US 8,263,778 B2
(45) Date of Patent: Sep. 11, 2012

(54) PROCESS FOR PRODUCING PYRIPYROPENE DERIVATIVES AND INTERMEDIATES FOR THE PRODUCTION THEREOF

(75) Inventors: Kimihiko Goto, Yokohama (JP); Kazumi Yamamoto, Kamakura (JP); Masayo Sakai, Yokohama (JP); Masaaki Mitomi, Yokosuka (JP); Takashi Ando, Yokohama (JP)

(73) Assignee: Meiji Seika Pharma Co., Ltd., Tokyo-To (JP)

(*) Notice: Subject to any disclaimer, the term of this patent is extended or adjusted under 35 U.S.C. 154(b) by 315 days.

(21) Appl. No.: 12/733,113

(22) PCT Filed: Aug. 13, 2008

(86) PCT No.: PCT/JP2008/064520
§ 371 (c)(1),
(2), (4) Date: Feb. 12, 2010

(87) PCT Pub. No.: WO2009/022702
PCT Pub. Date: Feb. 19, 2009

(65) Prior Publication Data
US 2010/0160640 A1 Jun. 24, 2010

(30) Foreign Application Priority Data
Aug. 13, 2007 (JP) ................. 2007-210804

(51) Int. Cl.
*C07D 493/04* (2006.01)
(52) U.S. Cl. .................................... 546/283.1
(58) Field of Classification Search ................ 546/283.1
See application file for complete search history.

(56) References Cited

U.S. PATENT DOCUMENTS
5,807,721 A 9/1998 Omura et al.
2006/0281780 A1 12/2006 Goto et al.

FOREIGN PATENT DOCUMENTS
| EP | 1 889 540 | 2/2008 |
| EP | 2 107 060 | 10/2009 |
| JP | 8-239385 | 9/1996 |
| JP | 8-259569 | 10/1996 |
| JP | 8-269065 | 10/1996 |
| WO | 2004/060065 | 7/2004 |
| WO | 2006/129714 | 12/2006 |
| WO | 2008/013336 | 1/2008 |

OTHER PUBLICATIONS

International Search Report issued Oct. 7, 2008 in International (PCT) Application No. PCT/JP2008/064520.
R. Obata et al., "Chemical Modification and Structure-Activity Relationships of Pyripyropenes 2. 1,11-Cyclic Analogs", Journal of Antibiotics, vol. 49, No. 11, pp. 1149-1156, Nov. 1996.
R. Obata et al., "Chemical Modification and Structure-Activity Relationships of Pyripyropenes; Potent, Bioavailable Inhibitor of Acyl-CoA: Cholesterol O-Acyltransferase(ACAT)", Bioorganic & Medicinal Chemistry Letters, vol. 5, No. 22, pp. 2683-2688, 1995.
R. Obata et al., "Chemical Modification and Structure-Activity Relationships of Pyripyropenes 1. Modification at the Four Hydroxyl Groups", The Journal of Antibiotics, vol. 49, No. 11, pp. 1133-1148, Nov. 1996.
H. Tomoda et al., "Pyripyropenes, Novel ACAT Inhibitors Produced by *Aspergillus fumigatus* III. Structure Elucidation of Pyripyropenes E to L", The Journal of Antibiotics, vol. 48, No. 6, pp. 495-503, 1995.
Supplementary European Search Report issued Dec. 22, 2011 in Application No. EP 08827512.8.

*Primary Examiner* — Patricia Morris
(74) *Attorney, Agent, or Firm* — Wenderoth, Lind & Ponack, L.L.P.

(57) ABSTRACT

Disclosed is a process for producing compound C represented by formula C:

[Chemical formula 1]

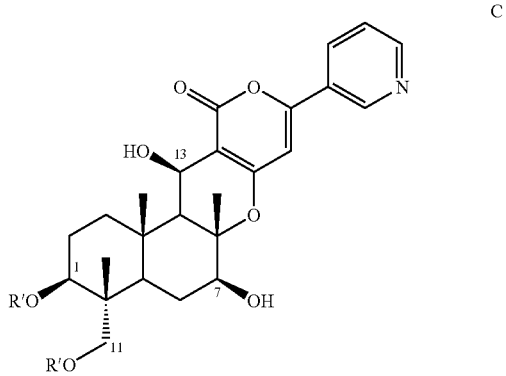

wherein R' represents straight chain, branched chain, or cyclic $C_{2-6}$ alkylcarbonyl, wherein $R_{1b}$ is used as a protective group for hydroxyl at the 7-position of compound C. $R_{1b}$ represents formyl; optionally substituted straight chain $C_{1-4}$ alkylcarbonyl; optionally substituted benzyl; group —$SiR_3R_4R_5$ optionally substituted by halogen atom wherein $R_3$, $R_4$, and $R_5$ each independently represent straight chain or branched chain $C_{1-6}$ alkyl or phenyl; $C_{1-6}$ alkyloxy-$C_{1-6}$ alkyl optionally substituted by halogen atom; $C_{1-6}$ alkylthio-$C_{1-6}$ alkyl optionally substituted by halogen atom; straight chain, branched chain, or cyclic $C_{1-4}$ alkyl optionally substituted by halogen atom, provided that, when alkyl in the $C_{1-4}$ alkyl group is of a branched chain or cyclic type, the alkyl group is $C_{3-4}$ alkyl; $C_{2-6}$ alkenyl optionally substituted by halogen atom; $C_{2-6}$ alkynyl optionally substituted by halogen atom; or an optionally substituted saturated or unsaturated five- or six-membered heterocyclic group. The process can produce pyripyropene derivatives that have acyloxy groups at the 1- and 11-positions and a hydroxyl group at the 7-position and are useful as insect pest control agents at a high yield.

3 Claims, No Drawings

PROCESS FOR PRODUCING PYRIPYROPENE DERIVATIVES AND INTERMEDIATES FOR THE PRODUCTION THEREOF

This application is a U.S. national stage of International Application No. PCT/JP2008/064520 filed Aug. 13, 2008.

CROSS-REFERENCE OF RELATED APPLICATION

This patent application is an application claiming priority based on a prior Japanese Patent Application, Japanese Patent Application No. 210804/2007 (filing date: Aug. 13, 2007). The whole disclosure of Japanese Patent Application No. 210804/2007 is incorporated herein by reference.

BACKGROUND OF THE INVENTION

1. Field of Invention

The present invention relates to a process for producing pyripyropene derivatives useful as pest control agents and more specifically relates to a process for producing pyripyropene derivatives that have acyloxy groups at the 1- and 11-positions and a hydroxyl group at the 7-position thereof.

2. Background Art

Pyripyropene derivatives having acyloxy at 1- and 11-positions and hydroxyl at the 7-position thereof are compounds that have control effects against pests, as described in WO 2006/129714.

WO 2006/129714 and Japanese Patent Application Laid-Open No. 259569/1996 disclose a process for producing pyripyropene derivatives having acyloxy at 1- and 11-positions and hydroxyl at the 7-position thereof. According to the production process, the pyripyropene derivatives are purified or isolated from a plurality of products produced by nonselective hydrolysis of acyloxy using a 1,7,11-triacyloxy compound as a starting compound. This production process, however, suffers from problems such as low yield and unsuitability for quantity synthesis.

Further, Japanese Patent Application Laid-Open No. 259569/1996 describes the use of a combination of protective groups for the synthesis of pyripyropene derivatives, and Journal of Antibiotics Vol. 49, No. 11, p. 1149, 1996, Bioorganic Medicinal Chemistry Letter Vol. 5, No. 22, p. 2683, 1995, Japanese Patent Application Laid-Open No. 269065/1996, and WO 2008/013336 disclose a synthesis example that introduces acyl into the 7-position by utilizing a protective group. These documents, however, do not disclose a specific process that utilizes a protective group in the production of pyripyropene derivatives that have acyloxy at the 1- and 11-positions and hydroxyl at the 7-position thereof.

SUMMARY OF THE INVENTION

The present inventors have found that pyripyropene derivatives having acyloxy groups at the 1- and 11-positions and a hydroxyl group at the 7-position thereof can be produced at high yield from pyripyropene A (Japanese Patent Application Laid-Open No. 259569/1996; Bioorganic Medicinal Chemistry Letter Vol. 5, No. 22, p. 2683, 1995; and WO2004/060065) which is obtained as a naturally occurring substance, by using a proper protective group. The present invention has been made based on such finding.

Accordingly, an object of the present invention is to provide a process for producing pyripyropene derivatives useful as pest control agents and to provide compounds as intermediates for the production of pyripyropene derivatives.

According to a first aspect of the present invention, there is provided a process for producing compound C represented by formula C:

[Chemical formula 1]

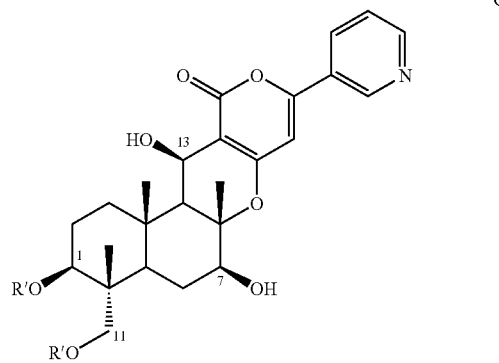

wherein R' represents straight chain, branched chain, or cyclic $C_{2-6}$ alkylcarbonyl, provided that, when the alkyl moiety in the alkylcarbonyl group is of a branched chain or cyclic type, R' represents $C_{3-6}$ alkylcarbonyl, the process comprising the steps of:

($a_1$) hydrolyzing acetyl at the 7-position of compound A1 represented by formula A1:

[Chemical formula 2]

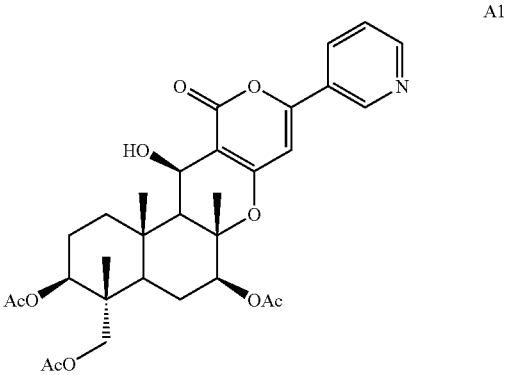

wherein Ac represents acetyl, with a base to selectively deacylate compound A1, then protecting hydroxyl at the 7-position to give compound B1 represented by formula B1:

[Chemical formula 3]

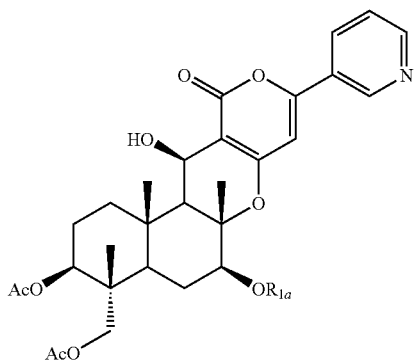

B1 wherein
Ac is as defined above,
$R_{1a}$ represents optionally substituted straight chain $C_{2-4}$ alkylcarbonyl; group —$SiR_3R_4R_5$ optionally substituted by halogen atom wherein $R_3$, $R_4$, and $R_5$ each independently represent straight chain or branched chain $C_{1-6}$ alkyl or phenyl; $C_{1-6}$ alkyloxy-$C_{1-6}$ alkyl optionally substituted by halogen atom; $C_{1-6}$ alkylthio-$C_{1-6}$ alkyl optionally substituted by halogen atom; straight chain, branched chain, or cyclic $C_{1-4}$ alkyl optionally substituted by halogen atom, provided that, when alkyl in the $C_{1-4}$ alkyl group is of a branched chain or cyclic type, the alkyl group represents $C_{3-4}$ alkyl; $C_{2-6}$ alkenyl optionally substituted by halogen atom; $C_{2-6}$ alkynyl optionally substituted by halogen atom; optionally substituted benzyl; or an optionally substituted saturated or unsaturated five- or six-membered heterocyclic group, wherein, in $R_{1a}$, the substituent optionally possessed by alkylcarbonyl is selected from the group consisting of halogen atoms, $C_{1-4}$ alkyloxy, $C_{1-4}$ haloalkyloxy, $C_{1-4}$ alkylcarbonyl, $C_{1-4}$ haloalkylcarbonyl, $C_{1-4}$ alkylcarbonyloxy, and $C_{1-4}$ haloalkylcarbonyloxy, and the substituent optionally possessed by the heterocyclic group and benzyl is selected from the group consisting of halogen atoms, $C_{1-4}$ alkyl, $C_{1-4}$ alkyloxy, $C_{1-4}$ haloalkyloxy, $C_{1-4}$ alkylthio, $C_{1-4}$ haloalkyl, $C_{1-4}$ alkylcarbonyl, $C_{1-4}$ haloalkylcarbonyl, $C_{1-4}$ alkylcarbonyloxy, $C_{1-4}$ haloalkylcarbonyloxy, nitro, and cyano, then hydrolyzing acetyl at the 1- and 11-positions of compound B1 with a base to deacylate compound B1 and thus to give compound Fa represented by formula Fa:

[Chemical formula 4]

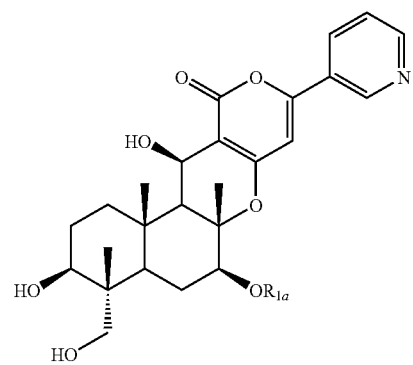

Fa wherein $R_{1a}$ is as defined above, or ($a_2$) hydrolyzing acyl at the 1-, 7-, and 11-positions of compound A1 or compound A4' represented by formula A4':

[Chemical formula 5]

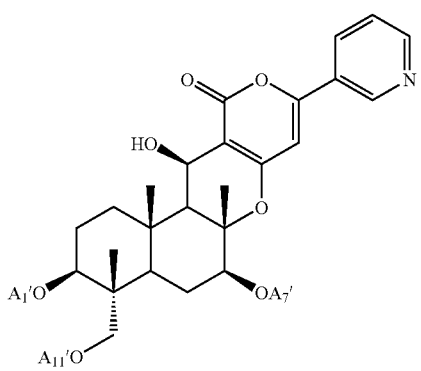

A4' wherein $A_1'$, $A_7'$, and $A_{11}'$, which may be the same or different, represent acetyl or propionyl, provided that $A_1'$, $A_7'$, and $A_{11}'$ do not simultaneously represent acetyl, with a base to deacylate compound A1 or A4' and then protecting hydroxyl at the 1- and 11-positions to give compound D represented by formula D:

[Chemical formula 6]

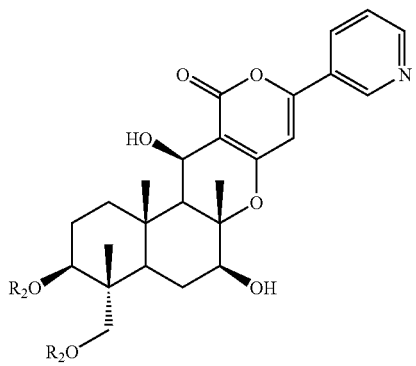

D wherein two $R_2$s together represent a group selected from groups represented by formulae D-1, D-2, D-3, and D-4:

[Chemical formula 7]

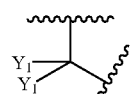

D-1

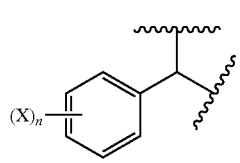

D-2

-continued

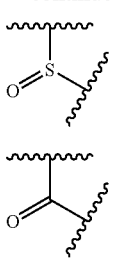
D-3

D-4 wherein $Y_1$ represents a hydrogen atom or $C_{1-4}$ alkyl; Xs, which may be the same or different, represent a hydrogen atom, $C_{1-4}$ alkoxy, or nitro; and n is 0 to 5, then protecting hydroxyl at the 7-position of compound D to give compound E represented by formula E:

[Chemical formula 8]

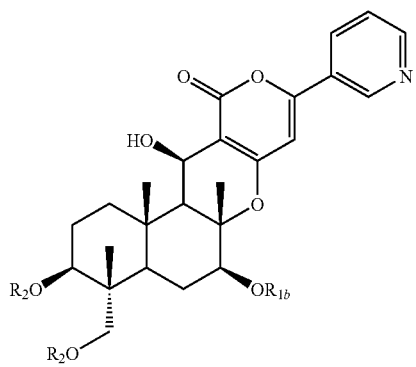
E wherein $R_{1b}$ represents formyl; optionally substituted straight chain $C_{1-4}$ alkylcarbonyl; optionally substituted benzyl; group —$SiR_3R_4R_5$ optionally substituted by halogen atom wherein $R_3$, $R_4$, and $R_5$ each independently represent straight chain or branched chain $C_{1-6}$ alkyl or phenyl; $C_{1-6}$ alkyloxy-$C_{1-6}$ alkyl optionally substituted by halogen atom; $C_{1-6}$ alkylthio-$C_{1-6}$ alkyl optionally substituted by halogen atom; straight chain, branched chain, or cyclic $C_{1-4}$ alkyl optionally substituted by halogen atom, provided that, when alkyl in the $C_{1-4}$ alkyl group is of a branched chain or cyclic type, the alkyl group is $C_{3-4}$ alkyl; $C_{2-6}$ alkenyl optionally substituted by halogen atom; $C_{2-6}$ alkynyl optionally substituted by halogen atom; or an optionally substituted saturated or unsaturated five- or six-membered heterocyclic group, wherein, in $R_{1b}$, the substituent optionally possessed by alkylcarbonyl is selected from the group consisting of halogen atoms, $C_{1-4}$ alkyloxy, $C_{1-4}$ haloalkyloxy, $C_{1-4}$ alkylcarbonyl, $C_{1-4}$ haloalkylcarbonyl, $C_{1-4}$ alkylcarbonyloxy, and $C_{1-4}$ haloalkylcarbonyloxy, and the substituent optionally possessed by the heterocyclic group and benzyl is selected from the group consisting of halogen atoms, $C_{1-4}$ alkyl, $C_{1-4}$ alkyloxy, $C_{1-4}$ haloalkyloxy, $C_{1-4}$ alkylthio, $C_{1-4}$ haloalkyl, $C_{1-4}$ alkylcarbonyl, $C_{1-4}$ haloalkylcarbonyl, $C_{1-4}$ alkylcarbonyloxy; $C_{1-4}$ haloalkylcarbonyloxy, nitro, and cyano, and $R_2$ is as defined above, and further removing the protective groups at the 1- and 11-positions of compound E to give compound Fb represented by formula Fb:

[Chemical formula 9]

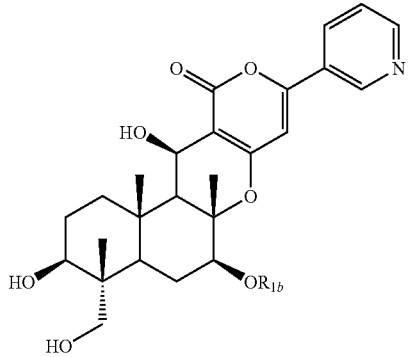
Fb wherein $R_{1b}$ is as defined above, and (b) acylating hydroxyl at the 1- and 11-positions of compound Fa or Fb with an acylating agent corresponding to contemplated R' to give compound B2a or B2b represented by formula B2a or B2b:

[Chemical formula 10]

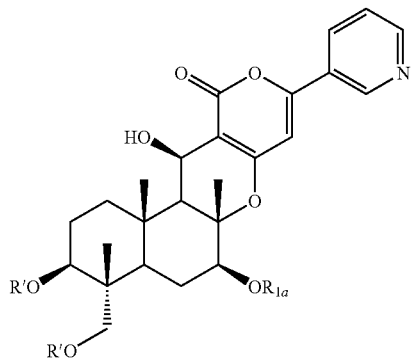
B2a

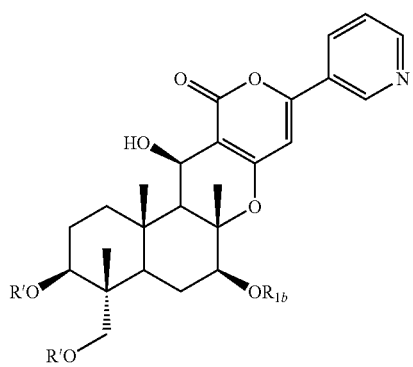
B2b wherein $R_{1a}$, $R_{1b}$, and R' are as defined above, and then removing the protective group at the 7-position of compound B2a or compound B2b.

According to a second aspect of the present invention, there is provided a process for producing compound B2a represented by formula B2a:

[Chemical formula 11]

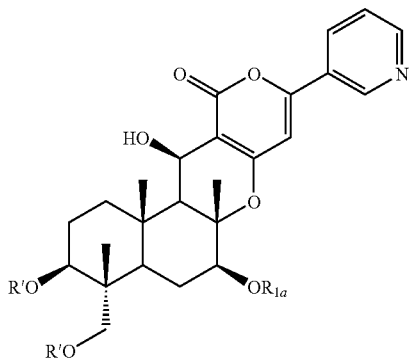

B2a wherein $R_{1a}$ is as defined above and R' represents cyclic $C_{3-6}$ alkylcarbonyl, the process comprising:

hydrolyzing acetyl at the 7-position of compound A1 described above with a base to selectively deacylate compound A1, then protecting hydroxyl at the 7-position to give compound B1 represented by formula B1:

[Chemical formula 12]

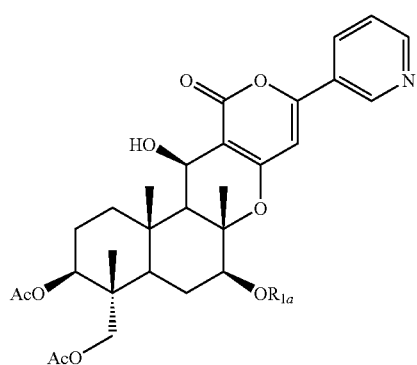

B1 wherein Ac and $R_{1a}$ are as defined above, then hydrolyzing acetyl at the 1- and 11-positions of compound B1 with a base to deacylate compound B1 and thus to give compound Fa represented by formula Fa:

[Chemical formula 13]

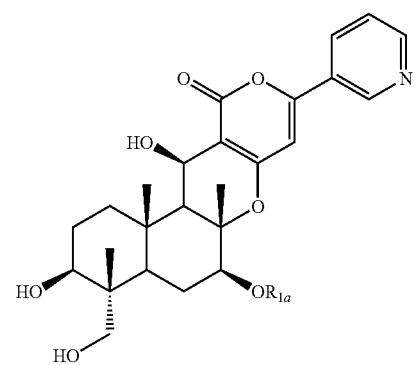

Fa wherein $R_{1a}$ is as defined above, and then acylating hydroxyl at the 1- and 11-positions of compound Fa with an acylating agent corresponding to contemplated R'.

According to a third aspect of the present invention, there is provided a process for producing compound B2b represented by formula B2b described above wherein R' represents cyclic $C_{3-6}$ alkylcarbonyl, the process comprising:

hydrolyzing acyl at the 1-, 7-, and 11-positions of compound A4 represented by formula A4:

[Chemical formula 14]

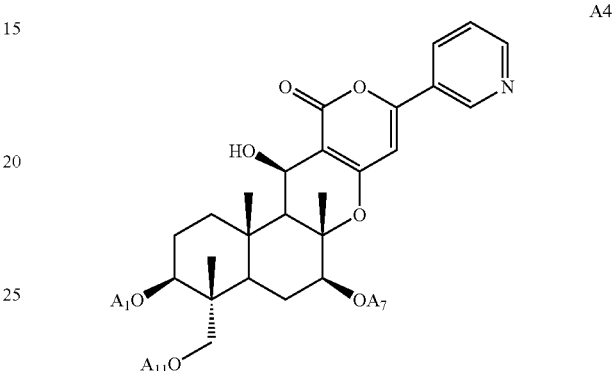

A4 wherein $A_1$, $A_7$, and $A_{11}$, which may be the same or different, represent acetyl or propionyl, with a base to deacylate compound A4, then protecting hydroxyl at the 1- and 11-positions to give compound D, then protecting hydroxyl at the 7-position of compound D to give compound E described above, further removing the protective group at the 1- and 11-positions of compound E to give compound Fb described above, and then acylating hydroxyl at the 1- and 11-positions of compound Fb with an acylating agent corresponding to R'.

According to a fourth aspect of the present invention, there is provided a process for producing compound C represented by formula C wherein R' represents cyclic $C_{3-6}$ alkylcarbonyl. The process comprises acylating hydroxyl at the 1- and 11-positions of compound Fb described above with an acylating agent corresponding to R' to give compound B2b and then removing the protective group at the 7-position of compound B2b.

According to a fifth aspect of the present invention, there is provided a process for producing compound C described above. The process comprises hydrolyzing acyl at the 1-, 7-, and 11-positions of compound A4 with a base to deacylate compound A4, then protecting hydroxyl at the 1- and 11-positions to give compound D, then protecting hydroxyl at the 7-position of compound D to give compound E, further removing the protective groups at the 1- and 11-positions of compound E to give compound Fb, then acylating hydroxyl at the 1- and 11-positions of compound Fb with an acylating agent corresponding to R' to give compound B2b, and then removing the protective group at the 7-position of compound B2b.

According to a sixth aspect of the present invention, there is provided a compound that has acyloxy at the 1- and 11-positions and hydroxyl at the 7-position and is useful as an intermediate for the production of pyripyropene derivatives. The compound is represented by formula B2b:

[Chemical formula 15]

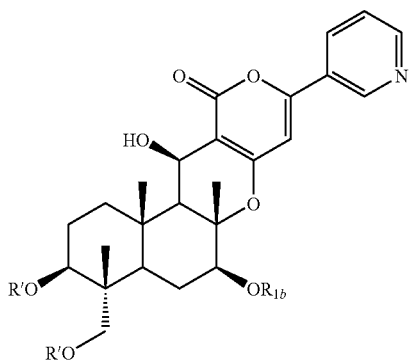

wherein $R_{1b}$ is as defined above; and R' represents cyclic $C_{3-6}$ alkylcarbonyl.

The present invention allows for producing pyripyropene derivatives that have acyloxy groups at the 1- and 11-positions and a hydroxyl group at the 7-position and are useful as pest control agents at high yield.

DETAILED DESCRIPTION OF THE INVENTION

The term "halogen" as used herein means fluorine, chlorine, bromine, or iodine.

The terms "alkyl," "alkenyl," or "alkynyl" as used herein as a substituent or a part of a substituent means alkyl, alkenyl, or alkynyl that is of a straight chain, branched chain, or cyclic type or a type of a combination thereof unless otherwise specified.

The symbol "$C_{a-b}$" attached to a substituent as used herein means that the number of carbon atoms contained in the substituent as used herein is a to b. Further, "$C_{a-b}$" in "$C_{a-b}$ alkylcarbonyl" means that the number of carbon atoms in the alkyl moiety excluding the carbon atoms in the carbonyl moiety is a to b.

The term "haloalkyl" as used herein means alkyl substituted by at least one halogen atom. Likewise, the terms "haloalkyloxy," "haloalkylcarbonyl," and "haloalkylcarbonyloxy" respectively mean alkyloxy substituted by at least one halogen atom, alkylcarbonyl substituted by at least one halogen atom, and alkylcarbonyloxy substituted by at least one halogen atom.

Specific examples of the straight chain, branched chain, or cyclic $C_{2-6}$ alkylcarbonyl group, represented by R', wherein, when the alkyl moiety in the $C_{2-6}$ alkylcarbonyl group is of a branched chain or cyclic type, the alkyl moiety is $C_{3-6}$ alkylcarbonyl, include cyclopropanecarbonyl and propionyl. The alkylcarbonyl group is preferably cyclic $C_{3-6}$ alkylcarbonyl, more preferably cyclopropanecarbonyl.

Specific examples of the group —$SiR_3R_4R_5$, wherein $R_3$, $R_4$, and $R_5$ each independently represent straight chain or branched chain $C_{1-6}$ alkyl or phenyl, represented by $R_{1a}$ and $R_{1b}$ include trimethylsilyl, triethylsilyl, triisopropylsilyl, tert-butyldimethylsilyl, and tert-butyldiphenylsilyl. The group —$SiR_3R_4R_5$ is optionally substituted, and such substituents include halogen atoms. In the group —$SiR_3R_4R_5$, preferably, all of $R_3$, $R_4$, and $R_5$ represent straight chain or branched chain $C_{1-6}$ alkyl, that is, the group —$SiR_3R_4R_5$ is preferably alkyl silyl, more preferably tert-butyldimethylsilyl.

Specific examples of the straight chain, branched chain, or cyclic $C_{1-4}$ alkyl group, represented by $R_{1a}$ and $R_{1b}$, wherein, when alkyl in the $C_{1-4}$ alkyl group is of a branched chain or cyclic type, the alkyl group is $C_{3-4}$ alkyl, include methyl, ethyl, propyl, i-propyl, cyclopropyl, n-butyl, i-butyl, and tert-butyl. The alkyl group is optionally substituted, and such substituents include halogen atoms.

Specific examples of the $C_{2-6}$ alkenyl group represented by $R_{1a}$ and $R_{1b}$ include vinyl, (1- or 2-)propenyl, (1-, 2-, or 3-)butenyl, (1-, 2-, 3-, or 4-)pentenyl, and (1-, 2-, 3-, 4-, or 5-)hexenyl. The alkenyl group is optionally substituted, and such substituents include halogen atoms.

Specific examples of the $C_{2-6}$ alkynyl group represented by $R_{1a}$ and $R_{1b}$ include ethynyl, (1- or 2-)propynyl, (1-, 2-, or 3-)butynyl, (1-, 2-, 3-, or 4-)pentynyl, and (1-, 2-, 3-, 4-, or 5-)hexynyl. The alkynyl group is optionally substituted, and such substituents include halogen atoms.

Specific examples of the saturated or unsaturated five- or six-membered heterocyclic group represented by $R_{1a}$ and $R_{1b}$ include tetrahydropyranyl, tetrahydrothiopyranyl, tetrahydrofuranyl, and tetrahydrothiofuranyl. The heterocyclic group is optionally substituted, and such substituents include halogen atoms, $C_{1-4}$ alkyl, $C_{1-4}$ alkyloxy, $C_{1-4}$ haloalkyloxy, $C_{1-4}$ alkylthio, $C_{1-4}$ haloalkyl, $C_{1-4}$ alkylcarbonyl, $C_{1-4}$ haloalkylcarbonyl, $C_{1-4}$ alkylcarbonyloxy, $C_{1-4}$ haloalkylcarbonyloxy, nitro, and cyano. The heterocyclic group is preferably tetrahydropyranyl.

Specific examples of the straight chain $C_{2-4}$ alkylcarbonyl group represented by $R_{1a}$ include propionyl, propylcarbonyl, and n-butylcarbonyl. The alkylcarbonyl group is optionally substituted, and such substituents include halogen atoms, $C_{1-4}$ alkyloxy, $C_{1-4}$ haloalkyloxy, $C_{1-4}$ alkylcarbonyl, $C_{1-4}$ haloalkylcarbonyl, $C_{1-4}$ alkylcarbonyloxy, and $C_{1-4}$ haloalkylcarbonyloxy.

Specific examples of the straight chain $C_{1-4}$ alkylcarbonyl group represented by $R_{1b}$ include acetyl, propionyl, propylcarbonyl, and n-butylcarbonyl. The alkylcarbonyl group is optionally substituted, and such substituents include halogen atoms, $C_{1-4}$ alkyloxy, $C_{1-4}$ haloalkyloxy, $C_{1-4}$ alkylcarbonyl, $C_{1-4}$ haloalkylcarbonyl, $C_{1-4}$ alkylcarbonyloxy, and $C_{1-4}$ haloalkylcarbonyloxy.

The $C_{1-6}$ alkyloxy-$C_{1-6}$ alkyl group represented by $R_{1a}$ and $R_{1b}$ is optionally substituted, and such substituents include halogen atoms.

The $C_{1-6}$ alkylthio-$C_{1-6}$ alkyl group represented by $R_{1a}$ and $R_{1b}$ is optionally substituted, and such substituents include halogen atoms.

The benzyl group represented by $R_{1a}$ and $R_{1b}$ is optionally substituted, and such substituents include halogen atoms, $C_{1-4}$ alkyl, $C_{1-4}$ alkyloxy, $C_{1-4}$ haloalkyloxy, $C_{1-4}$ alkylthio, $C_{1-4}$ haloalkyl, $C_{1-4}$ alkylcarbonyl, $C_{1-4}$ haloalkylcarbonyl, $C_{1-4}$ alkylcarbonyloxy, $C_{1-4}$ haloalkylcarbonyloxy, nitro, and cyano.

Preferably, $R_{1a}$ represents group —$SiR_3R_4R_5$ optionally substituted by halogen atom wherein $R_3$, $R_4$, and $R_5$ each independently represent straight chain or branched chain $C_{1-6}$ alkyl or phenyl; or an optionally substituted saturated or unsaturated five- or six-membered heterocyclic group, more preferably group —$SiR_3R_4R_5$ wherein $R_3$, $R_4$, and $R_5$ each independently represent straight chain or branched chain $C_{1-6}$ alkyl or phenyl; or a saturated or unsaturated five- or six-membered heterocyclic group, still more preferably group —$SiR_3R_4R_5$ wherein $R_3$, $R_4$, and $R_5$ each independently represent straight chain or branched chain $C_{1-6}$ alkyl or phenyl; or tetrahydropyranyl, most preferably tert-butyldimethylsilyl or tetrahydropyranyl.

Preferably, $R_{1b}$ represents acetyl, chloroacetyl, an optionally substituted saturated or unsaturated five- or six-membered heterocyclic group, or group —$SiR_3R_4R_5$ optionally substituted by halogen atom wherein $R_3$, $R_4$, and $R_5$ each independently represent straight chain or branched chain $C_{1-6}$ alkyl or phenyl, more preferably acetyl, chloroacetyl, or group —$SiR_3R_4R_5$ optionally substituted by halogen atom wherein $R_3$, $R_4$, and $R_5$ each independently represent straight chain or branched chain $C_{1-6}$ alkyl or phenyl, still more preferably acetyl, chloroacetyl, or tert-butyldimethylsilyl, most preferably acetyl or chloroacetyl.

The substituent represented by combining two $R_2$s together is preferably a group represented by formula D-1 or D-2:

[Chemical formula 16]

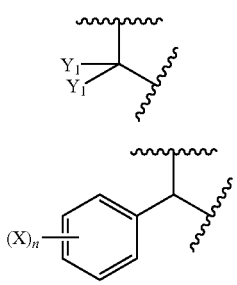

wherein $Y_1$ represents a hydrogen atom or $C_{1-4}$ alkyl; Xs, which may be the same or different, represent a hydrogen atom, $C_{1-4}$ alkoxy, or nitro; and n is 0 to 5, more preferably isopropylidene, benzylidene, or p-methoxybenzylidene. According to another embodiment, the substituent represented by combining two $R_2$s together is preferably D-1, more preferably isopropylidene.

Preferably, $A_1$, $A_7$, and $A_{11}$ each represent acetyl.

According to a preferred embodiment of the present invention, in the process according to the first aspect of the present invention or the process according to the fifth aspect of the present invention, R' represents cyclic $C_{3-6}$ alkylcarbonyl.

According to another preferred embodiment of the present invention, in the process according to the first aspect of the present invention, $R_{1a}$ represents group —$SiR_3R_4R_5$ optionally substituted by halogen atom wherein $R_3$, $R_4$, and $R_5$ each independently represent straight chain or branched chain $C_{1-6}$ alkyl or phenyl; or an optionally substituted saturated or unsaturated five- or six-membered heterocyclic group.

According to still another preferred embodiment of the present invention, in the process according to the first aspect of the present invention or the process according to the third aspect of the present invention, $R_{1b}$ represents acetyl, chloroacetyl, or group —$SiR_3R_4R_5$ optionally substituted by halogen atom wherein $R_3$, $R_4$, and $R_5$ each independently represent straight chain or branched chain $C_{1-6}$ alkyl or phenyl.

According to a further preferred embodiment of the present invention, in the process according to the first aspect of the present invention or the process according to the third aspect of the present invention, two $R_2$s together represent a group represented by formula D-1 or D-2:

[Chemical formula 17]

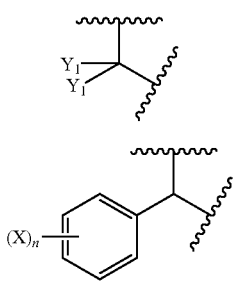

wherein $Y_1$ represents a hydrogen atom or $C_{1-4}$ alkyl; Xs, which may be the same or different, represent a hydrogen atom, $C_{1-4}$ alkoxy, or nitro; and n is 0 to 5.

According to a still further preferred embodiment of the present invention, in the process according to the second aspect of the present invention, $R_{1a}$ represents optionally substituted straight chain $C_{2-4}$ alkylcarbonyl; group —$SiR_3R_4R_5$ optionally substituted by halogen atom wherein $R_3$, $R_4$, and $R_5$ each independently represent straight chain or branched chain $C_{1-6}$ alkyl or phenyl; or an optionally substituted saturated or unsaturated five- or six-membered heterocyclic group.

According to another preferred embodiment of the present invention, in the compound according to the sixth aspect of the present invention, $R_{1b}$ represents acetyl, chloroacetyl, group —$SiR_3R_4R_5$ optionally substituted by halogen atom wherein $R_3$, $R_4$, and $R_5$ each independently represent straight chain or branched chain $C_{1-6}$ alkyl or phenyl, or an optionally substituted saturated or unsaturated five- or six-membered heterocyclic group; and R' represents cyclic $C_{3-6}$ alkylcarbonyl.

According to still another preferred embodiment of the present invention, in the process, R' in formulae B2a, B2b, and C represents propionyl or cyclopropanecarbonyl.

According to a further preferred embodiment of the present invention, in the process, the contemplated compound is produced through compound Fa wherein, in formula B1, Fa, or B2a, $R_{1a}$ represents optionally substituted straight chain or branched chain alkylsilyl or an optionally substituted saturated or unsaturated five- or six-membered heterocyclic group.

According to a still further preferred embodiment of the present invention, in the process, the contemplated compound is produced through compound Fb wherein $R_{1b}$ in formula E, Fb, or B2b represents acetyl, chloroacetyl, or optionally substituted straight chain or branched chain alkylsilyl.

According to another preferred embodiment of the present invention, in the process, the contemplated compound is produced through compound Fb wherein $R_2$ in formula D or E is a group represented by formula D-3.

According to a more preferred embodiment of the present invention, the contemplated compound is produced through compounds D, E, Fb, and B2b wherein $R_2$ in formula D or E represents a group represented by formula D-3; $R_{1b}$ in formula E, Fb, or B2b represents acetyl, chloroacetyl, or optionally substituted straight chain or branched chain alkylsilyl; and R' in formulae B2b and C represents cyclopropanecarbonyl.

According to another aspect of the present invention, there is provided a process for producing compound C represented by formula C:

[Chemical formula 18]

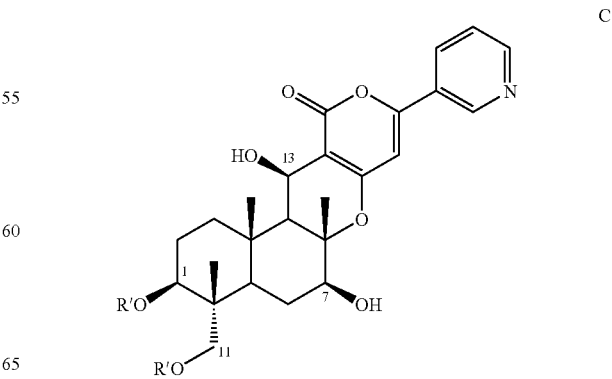

wherein R' represents cyclic $C_{3-6}$ alkylcarbonyl, the process comprising:

hydrolyzing acyl at the 1-, 7-, and 11-positions of compound A4 represented by formula A4:

[Chemical formula 19]

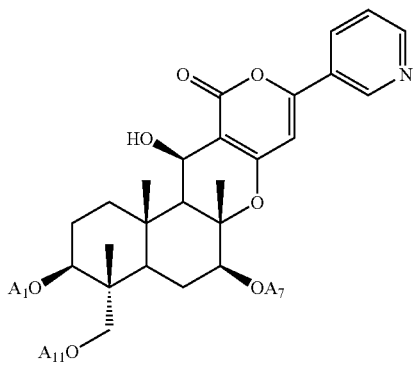

A4 wherein $A_1$, $A_7$, and $A_{11}$, which may be the same or different, represent acetyl or propionyl with a base to deacylate compound A4, then protecting hydroxyl at the 1- and 11-positions to give compound D represented by formula D:

[Chemical formula 20]

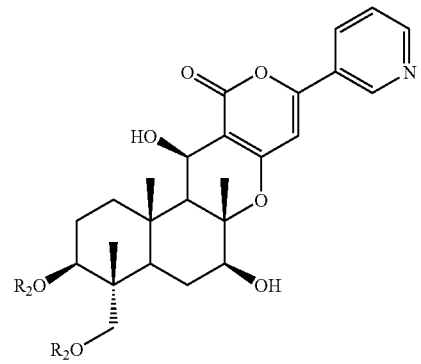

D wherein two $R_2$s together represent a group represented by formula D-1:

[Chemical formula 21]

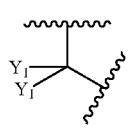

D-1 wherein $Y_1$ represents a hydrogen atom or $C_{1-4}$ alkyl, then protecting hydroxyl at the 7-position of compound D to give compound E represented by formula E:

[Chemical formula 22]

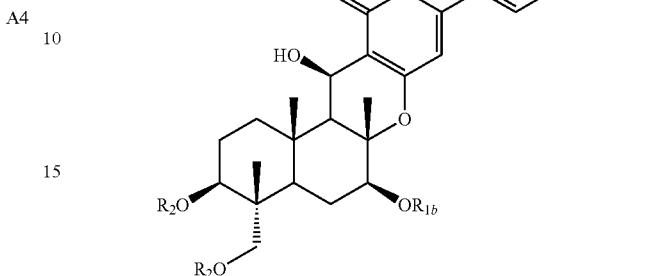

E wherein $R_{1b}$ represents acetyl or chloroacetyl and $R_2$ is as defined above, further removing the protective groups at the 1- and 11-positions of compound E to give compound Fb represented by formula Fb:

[Chemical formula 23]

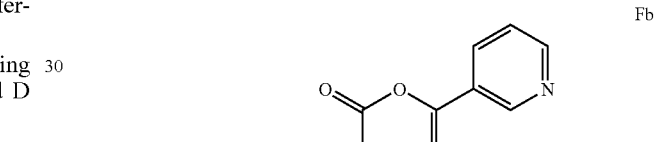

Fb then acylating hydroxyl at the 1- and 11-positions of compound Fb with an acylating agent corresponding to R' to give compound B2b represented by formula B2b:

[Chemical formula 24]

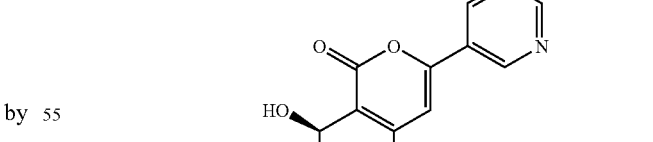

B2b wherein $R_{1b}$ and R' are as defined above,
and then removing the protective group at the 7-position of compound B2b.

The present invention will be described in detail according to the following scheme.
[Chemical formula 25]
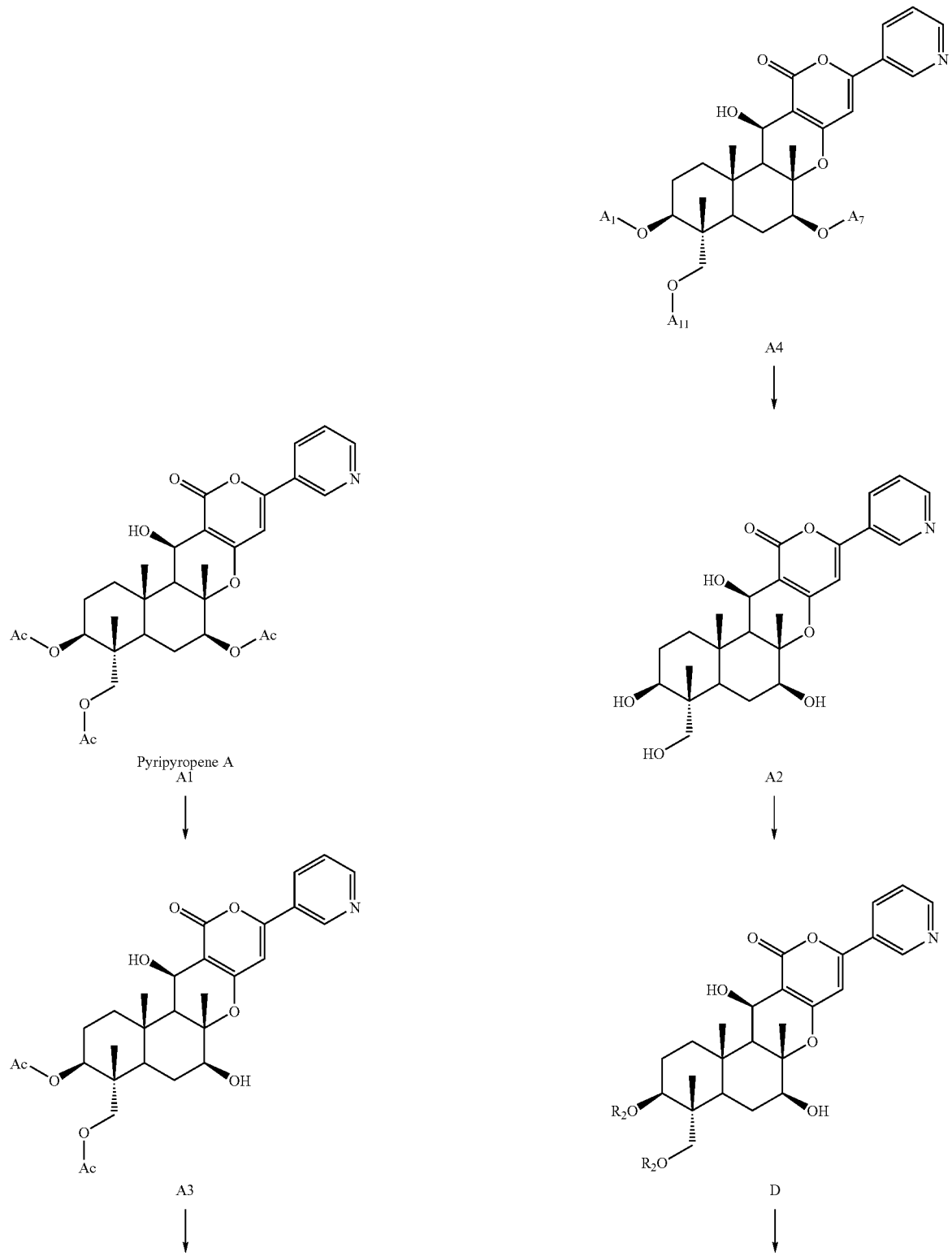

17
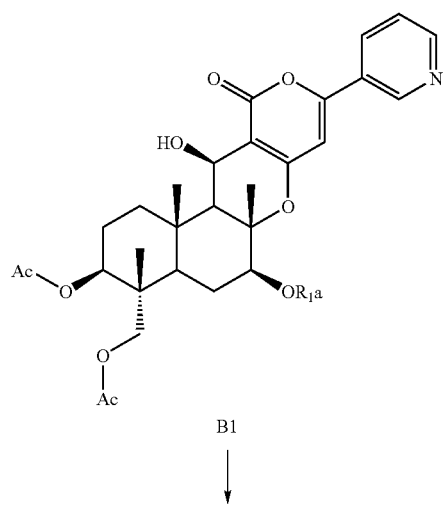
B1
↓
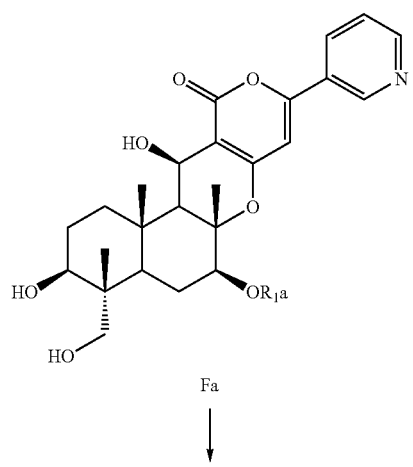
Fa
↓
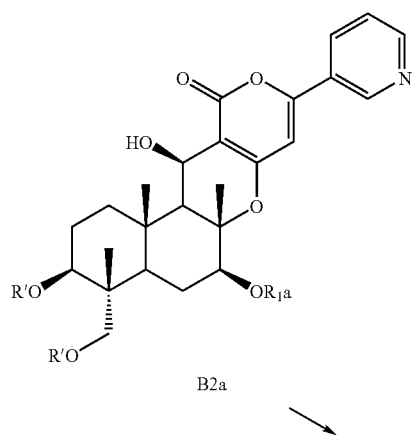
B2a
↓
-continued
18
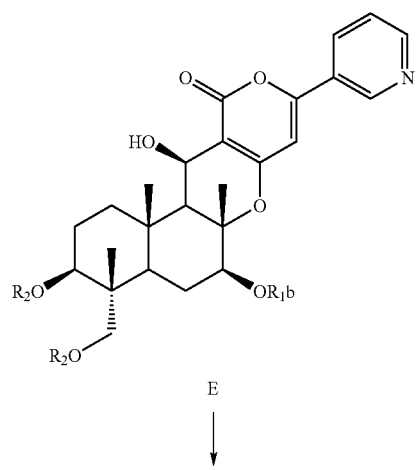
E
↓
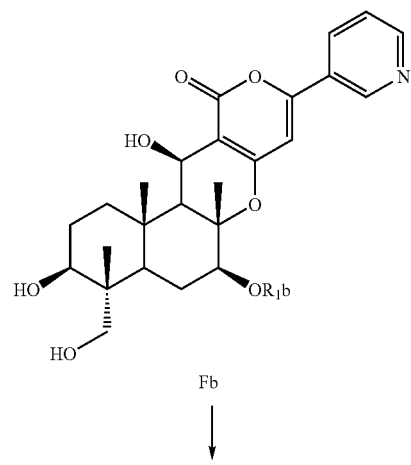
Fb
↓
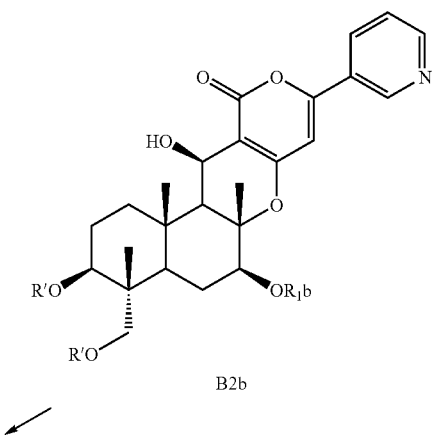
B2b
↓

-continued

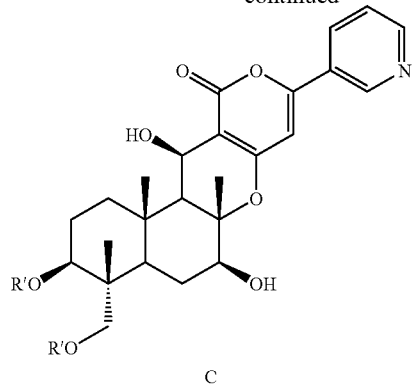

C

In the scheme, Ac, $R_{1a}$, $R_{1b}$, $A_1$, $A_7$, $A_{11}$, and $R_2$ are as defined above; R' represents straight chain, branched chain, or cyclic $C_{2-6}$ alkylcarbonyl wherein, when the alkyl moiety in the $C_{2-6}$ alkylcarbonyl group is of a branched chain or cyclic type, the alkyl moiety is $C_{3-6}$ alkylcarbonyl.

The product in each step may be used in a next step without post treatment.

1-1: Production of Compound A3 from Compound A1

Compound A1 can be produced by processes described, for example, in Japanese Patent Application Laid-Open No. 184158/1994, WO2004/060065, Japanese Patent Application Laid-Open No. 259569/1996, or Bioorganic Medicinal Chemistry Letter Vol. 5, No. 22, p. 2683.

Solvents usable in the step of producing compound A3 from compound A1 include alcohol solvents having 1 to 4 carbon atoms such as methanol, ether solvents such as diethyl ether, diisopropyl ether, tetrahydrofuran, and dioxane, aprotic polar organic solvents such as N,N-dimethylformamide, dimethylsulfoxide, N,N-dimethylacetamide, and acetonitrile, halogenated solvents such as dichloromethane and chloroform, or water, and mixed solvents composed of two or more of these solvents.

Bases usable herein include inorganic bases such as sodium carbonate, potassium carbonate, sodium hydrogen carbonate, potassium hydrogen carbonate, sodium hydroxide, potassium hydroxide, sodium hydride, potassium hydride, sodium cyanide, potassium cyanide, magnesium hydroxide, calcium hydroxide, lithium hydroxide, and barium hydroxide, alkali metals such as sodium methoxide, sodium ethoxide, and potassium tert-butoxide, alkoxides of alkaline earth metals, or organic bases such as 1,8-diazabicyclo[5.4.0]undeca-7-ene, 1,5-diazabicyclo[4.3.0]nona-5-ene, triethylamine, diisopropylethylamine, pyridine, hydrazine, and guanidine. Preferred are 1,8-diazabicyclo[5.4.0]undeca-7-ene, 1,5-diazabicyclo[4.3.0]nona-5-ene, sodium carbonate, potassium carbonate, sodium hydrogen carbonate, potassium hydrogen carbonate, sodium hydroxide, potassium hydroxide, sodium methoxide, and potassium tert-butoxide. Particularly preferred are 1,8-diazabicyclo[5.4.0]undeca-7-ene and potassium tert-butoxide.

The amount of the base used is preferably 0.01 to 1.2 equivalents based on the amount of compound A1. The reaction temperature is preferably −20° C. to 50° C. The reaction time is preferably 0.5 hr to seven days.

1-2: Production of Compound B1 from Compound A3

In the step of producing compound B1 from compound A3, hydroxyl at the 7-position can be protected by using a halide of $R_{1a}$ represented by $R_{1a}$-Hal, wherein Hal represents halogen atom, an acid anhydride of $R_{1a}$, or a mixed acid anhydride of $R_{1a}$, corresponding to contemplated $R_{1a}$, or 3,4-dihydropyran in the presence of a base, in the presence of an acid, or in the absence of a base and an acid, or using a condensing agent such as dicyclohexylcarbodiimide, 1-ethyl-3-(3-dimethylaminopropyl)carbodiimide hydrochloride, carbonyldiimidazole, dipyridyl disulfide, diimidazoyl disulfide, 1,3,5-trichlorobenzoyl chloride, 1,3,5-trichlorobenzoyl anhydride, PyBop, or PyBrop.

This step may be carried out in the absence or presence of a solvent. Solvents usable herein include ketone solvents such as acetone and diethyl ketone, ether solvents such as diethyl ether, diisopropyl ether, and tetrahydrofuran, ester solvents such as ethyl acetate and butyl acetate, aprotic polar organic solvents such as N,N-dimethylformamide, N,N-dimethylacetamide, dimethylsulfoxide, and acetonitrile, polar organic solvents such as pyridine, halogenated hydrocarbon solvents such as dichloromethane and chloroform, or aromatic hydrocarbon solvents such as toluene, and mixed solvents composed of two or more of these solvents.

Bases usable herein include, for example, sodium carbonate, potassium carbonate, sodium hydride, potassium tert-butoxide, sodium methoxide, sodium ethoxide, pyridine, dimethylaminopyridine, imidazole, 1,8-diazabicyclo[5.4.0]undeca-7-ene, 1,5-diazabicyclo[4.3.0]nona-5-ene, triethylamine, or diisopropylethylamine.

Acids usable herein include, for example, p-toluenesulfonic acid, p-toluenesulfonic acid monohydrate, pyridinium p-toluenesulfonate, 10-camphorsulfonic acid, hydrochloric acid, or sulfuric acid.

The reaction temperature is preferably −20° C. to 50° C. The reaction time is preferably 0.5 hr to four days.

1-3: Production of Compound Fa from Compound B1

Solvents usable in the step of producing compound Fa from compound B1 include alcohol solvents having 1 to 4 carbon atoms such as methanol, ether solvents such as diethyl ether, diisopropyl ether, tetrahydrofuran, and dioxane, aprotic polar organic solvents such as N,N-dimethylformamide, dimethylsulfoxide, N,N-dimethylacetamide, and acetonitrile, halogenated solvents such as dichloromethane and chloroform, or water, and mixed solvents composed of two or more of these solvents.

Bases usable herein include inorganic bases such as sodium carbonate, potassium carbonate, sodium hydrogen carbonate, potassium hydrogen carbonate, sodium hydroxide, potassium hydroxide, sodium hydride, potassium hydride, sodium cyanide, potassium cyanide, magnesium hydroxide, calcium hydroxide, lithium hydroxide, and barium hydroxide, alkali metals such as sodium methoxide, sodium ethoxide, and potassium tert-butoxide, alkoxides of alkaline earth metals, or organic bases such as 1,8-diazabicyclo[5.4.0]undeca-7-ene, 1,5-diazabicyclo[4.3.0]nona-5-ene, triethylamine, diisopropylethylamine, pyridine, hydrazine, and guanidine. Preferred are 1,8-diazabicyclo[5.4.0]undeca-7-ene, 1,5-diazabicyclo[4.3.0]nona-5-ene, sodium carbonate, potassium carbonate, sodium hydrogen carbonate, potassium hydrogen carbonate, sodium hydroxide, and potassium hydroxide. Particularly preferred is potassium carbonate.

The amount of the base used is preferably 0.01 to 10 equivalents based on the amount of compound B1. The reaction temperature is preferably −20° C. to 50° C. The reaction time is preferably 0.5 to 48 hr.

2-1: Production of Compound A2 from Compound A4

Compound A4 and compound A4' may be naturally occurring substances obtained by processes described, for example, in Japanese Patent Application Laid-Open No. 184158/1994, WO94/09147, and Japanese Patent Application Laid-Open No. 239385/1996. Alternatively, for example, derivatives obtained by a process described, for example, in Japanese Patent Application Laid-Open No. 259569/1996.

Solvents usable in the step of producing compound A2 from compound A4 include alcohol solvents having 1 to 4 carbon atoms such as methanol, ether solvents such as diethyl ether, diisopropyl ether, tetrahydrofuran, and dioxane, aprotic polar organic solvents such as N,N-dimethylformamide, dimethylsulfoxide, N,N-dimethylacetamide, and acetonitrile, halogenated solvents such as dichloromethane and chloroform, or water, and mixed solvents composed of two or more of these solvents.

Bases usable herein include inorganic bases such as sodium carbonate, potassium carbonate, sodium hydrogen carbonate, potassium hydrogen carbonate, sodium hydroxide, potassium hydroxide, sodium hydride, potassium hydride, sodium cyanide, potassium cyanide, magnesium hydroxide, calcium hydroxide, lithium hydroxide, and barium hydroxide, alkali metals such as sodium methoxide, sodium ethoxide, and potassium tert-butoxide, alkoxides of alkaline earth metals, or organic bases such as 1,8-diazabicyclo[5.4.0]undeca-7-ene, 1,5-diazabicyclo[4.3.0]nona-5-ene, triethylamine, diisopropylethylamine, pyridine, hydrazine, and guanidine. Preferred are 1,8-diazabicyclo[5.4.0]undeca-7-ene, 1,5-diazabicyclo[4.3.0]nona-5-ene, sodium carbonate, potassium carbonate, sodium hydrogen carbonate, potassium hydrogen carbonate, sodium hydroxide, and potassium hydroxide. Particularly preferred is potassium carbonate.

The amount of the base used is preferably 0.01 to 10 equivalents based on the amount of compound A4. The reaction temperature is preferably −20° C. to 50° C. The reaction time is preferably 0.5 to 48 hr.

According to this step, compound A2 can be likewise produced from compound A1 or compound A4' (compounds which are the same as compound A4, except that $A_1$, $A_7$, and $A_{11}$ in compound A4 are $A_1'$, $A_7'$, and $A_{11}'$, respectively).

2-2: Production of Compound E Through Compound D from Compound A2

Solvents usable in the step of producing compound D from compound A2 include ketone solvents such as acetone and diethyl ketone, ether solvents such as diethyl ether, diisopropyl ether, dioxane, and tetrahydrofuran, ester solvents such as ethyl acetate and butyl acetate, aprotic polar organic solvents such as N,N-dimethylformamide, N,N-dimethylacetamide, dimethylsulfoxide, and acetonitrile, halogenated hydrocarbon solvents such as dichloromethane and chloroform, or aromatic hydrocarbon solvents such as toluene, and mixed solvents composed of two or more of these solvents.

Hydroxyl at 1- and 11-positions can be protected by using, for example, dimethoxypropane, acetone, optionally substituted benzaldehyde or a dimethyl acetal form thereof, 2-methoxypropene, 2-ethoxypropene, phosgene, triphosgene, trichloroacetyl chloride, p-nitrobenzyloxycarbonyl chloride, or carbonyldiimidazole corresponding to contemplated $R_2$. Further, preferably, an acid catalyst such as p-toluenesulfonic acid, p-toluenesulfonic acid monohydrate, pyridinium p-toluenesulfonate, 10-camphorsulfonic acid, hydrogen fluoride, hydrochloric acid, hydrogen bromide, sulfuric acid, iodine, iron chloride, tin chloride, zinc chloride, aluminum chloride, trimethylchlorosilane, trimethylsilyltriflate, or 2,3-dichloro-5,6-dicyano-1,4-benzoquinone (preferably pyridinium p-toluenesulfonate and p-toluenesulfonic acid) is used in an amount of 0.001 to 20 equivalents, more preferably 0.01 to 5 equivalents, still more preferably 0.01 to 0.04 equivalent, based on compound A2.

The reaction temperature is preferably −20° C. to 50° C., more preferably room temperature to 50° C. The reaction time is preferably 0.5 to 48 hr.

More specifically, for example, compounds D and E which are compounds wherein $R_2$ represents D-1 can be produced by allowing a reaction to proceed using a protective group introducing reagent such as dimethoxypropane, 2-methoxypropene, or 2-ethoxypropene in the presence of an acid catalyst such as p-toluenesulfonic acid, p-toluenesulfonic acid monohydrate, pyridinium p-toluenesulfonate, or 10-camphorsulfonic acid in an amount of 0.001 to 20 equivalents, preferably 0.01 to 5 equivalents, more preferably 0.01 to 0.04 equivalent based on compound A2, or by allowing a reaction to proceed using p-toluenesulfonic acid, pyridinium p-toluenesulfonate, sulfuric acid, or copper sulfate in an amount of 0.001 to 20 equivalents based on compound A2 in an acetone solvent.

Compounds D and E which are compounds wherein $R_2$ represents D-2 can be produced by allowing a reaction to proceed using an optionally substituted benzaldehyde or a dimethyl acetal form thereof in the presence of an acid catalyst such as p-toluenesulfonic acid, p-toluenesulfonic acid monohydrate, pyridinium p-toluenesulfonate, or zinc chloride in an amount of 0.001 to 20 equivalents based on compound A2.

Next, the step of producing compound E from compound D can be carried out in the absence or presence of a solvent. Solvents usable herein include ketone solvents such as acetone, diethyl ketone, ether solvents such as diethyl ether, diisopropyl ether, dioxane, and tetrahydrofuran, ester solvents such as ethyl acetate and butyl acetate, aprotic polar organic solvents such as N,N-dimethylformamide, dimethylsulfoxide, N,N-dimethylacetamide, and acetonitrile, polar organic solvents such as pyridine, halogenated hydrocarbon solvents such as dichloromethane and chloroform, or aromatic hydrocarbon solvents such as toluene, and mixed solvents composed of two or more of these solvents.

A protective group corresponding to $R_{1b}$ can be introduced into hydroxyl at the 7-position by using a halide of $R_{1b}$ represented by $R_{1b}$-Hal, $R_{1b}$OH, $R_{1b}$Cl, $(R_{1b})_2$O, a mixed acid anhydride of $R_{1b}$, or 3,4-dihydropyran in the presence of a base, in the presence of an acid, or in the absence of a base and an acid, or using a condensing agent such as dicyclohexylcarbodiimide, 1-ethyl-3-(3-dimethylaminopropyl)carbodiimide hydrochloride, carbonyldiimidazole, dipyridyl disulfide, diimidazoyl disulfide, 1,3,5-trichlorobenzoyl chloride, 1,3,5-trichlorobenzoyl anhydride, PyBop, or PyBrop.

Bases usable herein include, for example, sodium carbonate, potassium carbonate, sodium hydride, potassium tert-butoxide, sodium methoxide, sodium ethoxide, pyridine, dimethylaminopyridine, imidazole, 1,8-diazabicyclo[5.4.0]undeca-7-ene, 1,5-diazabicyclo[4.3.0]nona-5-ene, triethylamine, or diisopropylethylamine.

Acids usable herein include, for example, p-toluenesulfonic acid, p-toluenesulfonic acid monohydrate, pyridinium p-toluenesulfonate, 10-camphorsulfonic acid, hydrochloric acid, or sulfuric acid.

The reaction temperature is preferably −20° C. to 50° C. The reaction time is preferably 0.5 hr to seven days.

More specifically, for example, a compound wherein $R_{1b}$ represents straight chain $C_{1-4}$ alkylcarbonyl optionally substituted by halogen atom, for example, acetyl or chloroacetyl can be produced by allowing a reaction to proceed using $R_{1b}$Cl or $(R_{1b})_2$O in an amount of 1 to 20 equivalents based on compound D and pyridine, dimethylaminopyridine, or triethylamine as a base in an amount of 0.1 to 20 equivalents based on compound D in the absence of a solvent or in tetrahydrofuran, dichloromethane, N,N-dimethylformamide, or pyridine or in a mixed solvent composed of two or more of these solvents at −20° C. to 50° C.

A compound wherein $R_{1b}$ represents group —$SiR_3R_4R_5$ optionally substituted by halogen atom wherein $R_3$, $R_4$, and $R_5$ each independently represent straight chain or branched chain $C_{1-6}$ alkyl or phenyl can be produced by allowing a reaction to proceed using a halide of $R_{1b}$ in an amount of 1 to 10 equivalents based on compound D and imidazole as a base in an amount of 1 to 10 equivalents based on compound D in dichloromethane, chloroform, N,N-dimethylformamide, N,N-dimethylacetamide, or a mixed solvent composed of two or more of these solvents at −20° C. to 50° C.

2-3: Production of Compound Fb from Compound E

Solvents usable in the step of producing compound Fb from compound E include alcohol solvents having 1 to 4 carbon atoms such as methanol, ketone solvents such as acetone and diethyl ketone, ether solvents such as diethyl ether, diisopropyl ether, tetrahydrofuran, and dioxane, aprotic polar organic solvents such as N,N-dimethylformamide, dimethylsulfoxide, N,N-dimethylacetamide, and acetonitrile, halogenated solvents such as dichloromethane and chloroform, or water, and mixed solvents composed of two or more of these solvents.

In the deprotection of the $R_2$ moiety, an organic acid such as acetic acid, trifluoroacetic acid, trifluoroacetic anhydride, hydrogen fluoride, hydrochloric acid, hydrogen bromide, sulfuric acid, p-toluenesulfonic acid, p-toluenesulfonic acid monohydrate, pyridinium p-toluenesulfonate, or 10-camphorsulfonic acid, or a hydrogenation catalyst such as boron chloride, magnesium bromide, dinitro zinc, bismuth chloride, cerium chloride, iron chloride, tin chloride, zinc chloride, aluminum chloride, palladium-carbon, or palladium hydroxide can be used, depending upon the type of the protective group, in an amount of 0.01 to 20 equivalents based on compound E.

The reaction temperature is preferably −20° C. to 50° C. The reaction time is preferably 0.5 to 48 hr.

More specifically, for example, when $R_2$ in compound E represents D-1, compound Fb can be produced by allowing a reaction to proceed using 0.01 to 20 equivalents, based on compound E, of hydrochloric acid, acetic acid, p-toluenesulfonic acid, p-toluenesulfonic acid monohydrate, pyridinium p-toluenesulfonate, or dinitro zinc, bismuth chloride (preferably hydrochloric acid, acetic acid, or pyridinium p-toluenesulfonate) in water, methanol, tetrahydrofuran, dichloromethane, chloroform, N,N-dimethylformamide, acetonitrile, or acetic acid or a mixed solvent composed of two or more of these solvents at −20° C. to 50° C., preferably at room temperature to 40° C.

When $R_2$ represents D-2, compound Fb can be produced by allowing a reaction to proceed using 0.01 to 20 equivalents, based on compound E, of 10-camphorsulfonic acid in water, methanol, tetrahydrofuran, or chloroform or a mixed solvent composed of two or more of these solvents at −20° C. to 50° C., preferably at room temperature to 40° C.

3: Production of Compound B2a from Compound Fa and Production of Compound B2b from Compound Fb The step of producing compound B2a from compound Fa and the step of producing compound B2b from compound Fb can be carried out in the absence or presence of a solvent. Solvents usable herein include ketone solvents such as acetone and diethyl ketone, ether solvents such as diethyl ether, diisopropyl ether, and tetrahydrofuran, ester solvents such as ethyl acetate and butyl acetate, aprotic polar organic solvents such as N,N-dimethylformamide, N,N-dimethylacetamide, dimethylsulfoxide, and acetonitrile, halogenated hydrocarbon solvents such as dichloromethane and chloroform, or aromatic hydrocarbon solvents such as toluene, and mixed solvents composed of two or more of these solvents.

Group R' can be introduced into the 1- and 11-position by using R'OH, R'Cl, (R')$_2$O, or a mixed acid anhydride corresponding to contemplated R' in the presence or absence of a base or using a condensing agent such as dicyclohexylcarbodiimide, 1-ethyl-3-(3-dimethylaminopropyl)carbodiimide hydrochloride, carbonyldiimidazole, dipyridyl disulfide, diimidazoyl disulfide, 1,3,5-trichlorobenzoyl chloride, 1,3,5-trichlorobenzoyl anhydride, PyBop, or PyBrop.

Bases usable herein include, for example, sodium carbonate, potassium carbonate, sodium hydride, potassium tert-butoxide, sodium methoxide, sodium ethoxide, pyridine, 4-dimethylaminopyridine, imidazole, 1,8-diazabicyclo [5.4.0]undeca-7-ene, 1,5-diazabicyclo[4.3.0]nona-5-ene, triethylamine, and diisopropylethylamine (preferably pyridine).

The reaction temperature is preferably −20° C. to 50° C., more preferably 0° C. to 30° C. The reaction time is preferably 0.5 to 48 hr.

4: Production of Compound C from Compound B2a or Compound B2b

Solvents usable in the step of producing compound C from compound B2a or B2b include alcohol solvents having 1 to 4 carbon atoms such as methanol, ether solvents such as diethyl ether, diisopropyl ether, tetrahydrofuran, and dioxane, aprotic polar organic solvents such as N,N-dimethylformamide, N,N-dimethylacetamide, dimethylsulfoxide, and acetonitrile, halogenated hydrocarbon solvents such as dichloromethane and chloroform, aromatic hydrocarbon solvents such as toluene, or water, and mixed solvents composed of two or more of these solvents.

The deprotection of $R_{1b}$ in compound B2b can be carried out depending upon the type of the protective group. For example, when $R_{1b}$ represents formyl, acetyl, or chloroacetyl, for example, an inorganic base such as sodium carbonate, potassium carbonate, sodium hydrogen carbonate, potassium hydrogen carbonate, sodium hydroxide, potassium hydroxide, sodium hydride, potassium hydride, sodium cyanide, potassium cyanide, magnesium hydroxide, calcium hydroxide, lithium hydroxide, or barium hydroxide, an alkali metal such as sodium methoxide, sodium ethoxide, or potassium tert-butoxide, an alkoxide of an alkaline earth metal, an organic base such as 1,8-diazabicyclo[5.4.0]undeca-7-ene, 1,5-diazabicyclo[4.3.0]nona-5-ene, triethylamine, diisopropylethylamine, pyridine, hydrazine, or guanidine, preferably sodium methoxide, sodium hydroxide, sodium carbonate, or sodium hydrogen carbonate can be used as a base in an amount of 0.01 to 10 equivalents, preferably 0.1 to 2 equivalents, based on compound B2b.

When $R_{1b}$ represents $C_{1-6}$ alkyloxy-$C_{1-6}$ alkyl optionally substituted by halogen atom, $C_{1-6}$ alkylthio-$C_{1-6}$ alkyl optionally substituted by halogen atom, straight chain, branched chain, or cyclic $C_{1-4}$ alkyl optionally substituted by halogen atom, $C_{2-6}$ alkenyl optionally substituted by halogen atom, $C_{2-6}$ alkynyl optionally substituted by halogen atom, an optionally substituted saturated or unsaturated five- or six-membered heterocyclic ring, optionally substituted benzyl, or group —$SiR_3R_4R_5$ optionally substituted by halogen atom, for example, an organic acid such as p-toluenesulfonic acid, p-toluenesulfonic acid monohydrate, pyridinium p-toluenesulfonate, hydrogen fluoride-pyridine, trihydrogen fluoride-triethylamine, acetic acid, acetic acid chloride, trifluoroacetic acid, trifluoroacetic anhydride, hydrogen fluoride, hydrochloric acid, hydrogen bromide, sulfuric acid, thiophenol, or 10-camphorsulfonic acid, a hydrogenation catalyst such as boron chloride, boron bromide, magnesium bromide, cerium chloride, copper chloride, copper sulfate, lithium chloride, iron chloride, tin chloride, zinc chloride, zinc bromide, aluminum chloride, titanium chloride, palladium-carbon, palladium hydroxide, or palladium chloride, trimethylchlorosilane, trimethyliodosilane, trimethylsilyltriflate, or 2,3-dichloro-5,6-dicyano-1,4-benzoquinone may be used in an amount of 0.1 to 10 equivalents based on compound B2b.

The reaction temperature is preferably −20° C. to 50° C., more preferably 0° C. to room temperature. The reaction time is preferably 0.5 hr to seven days.

According to this step, compound C can be likewise produced from compound B2a.

EXAMPLES

The present invention is further illustrated by the following Examples that are not intended as a limitation of the invention.

Example 1

Synthesis of 7-deacetylpyripyropene A

Pyripyropene A (30 mg) was dissolved in an 80% aqueous methanol solution (2 mL). 1,8-Diazabicyclo[5.4.0]-undeca-7-ene (9 mg) was added to the solution, and the mixture was stirred at room temperature for 1.5 hr. Acetic acid was added to the reaction solution to stop the reaction. The solvent was then removed by evaporation under the reduced pressure, water was added to the residue, and the mixture was extracted with ethyl acetate. The ethyl acetate layer was washed with saturated brine and was dried over anhydrous magnesium sulfate. The solvent was then removed by evaporation under the reduced pressure to give a crude product of 7-deacetylpyripyropene A. The crude product was purified by preparative thin-layer column chromatography (Merck silica gel 60F$_{254}$ 0.5 mm, acetone:hexane=1:1) to give 7-deacetylpyripyropene A (17 mg, yield 61%). The results of measurement by ESI-MS and $^1$H-NMR showed that the compound was PR-7 described in Japanese Patent Application Laid-Open No. 259569/1996.

Example 2

Synthesis of 7-O-tert-butyldimethylsilyl-7-deacetylpyripyropene A

7-Deacetylpyripyropene A (30 mg) synthesized by the process described in Example 1 was dissolved in N,N-dimethylformamide (5 mL), and imidazole (113 mg) and tert-butyldimethylchlorosilane (250 mg) were added to the solution. The mixture was stirred at room temperature for 24 hr. The reaction solution was then poured into water, and the mixture was extracted with ethyl acetate. The ethyl acetate layer was washed with saturated brine and was dried over anhydrous magnesium sulfate, and the solvent was then removed by evaporation under the reduced pressure to give a crude product of 7-O-tert-butyldimethylsilyl-7-deacetylpyripyropene A (470 mg).

ESI-MS: m/z 656 (M+H)$^+$;
$^1$H-NMR (CDCl$_3$): δ 0.11 (3H, s), 0.16 (3H, s), 0.90 (3H, s), 0.96 (9H, s), 1.30-1.38 (1H, m), 1.32-1.37 (1H, m), 1.41 (3H, s), 1.60 (3H, s), 1.61-1.69 (2H, m), 1.77-1.92 (1H, m), 2.05 (6H, s), 2.15 (1H, m), 2.89 (1H, d, J=2.4 Hz), 3.64-3.70 (2H, m), 3.73 (1H, d, J=11.6 Hz), 3.83 (1H, d, J=11.6 Hz), 4.78 (1H, dd, J=4.8, 11.2 Hz), 4.99 (1H, m), 6.36 (1H, s), 7.42 (1H, dd, J=4.8, 8.0 Hz), 8.11 (1H, d, J=8.0 Hz), 8.70 (1H, d, J=4.4 Hz), 9.00 (1H, d, J=2.0 Hz).

Example 3

Synthesis of 7-O-tert-butyldimethylsilyl-1,7,11-trideacetylpyripyropene A

7-O-tert-butyldimethylsilyl-7-deacetylpyripyropene A (470 mg) produced in Example 2 was dissolved in an 88% aqueous methanol solution (40 mL). Potassium carbonate (307 mg) was added to the solution, and the mixture was stirred at room temperature for 19.5 hr. The solvent was removed by evaporation under the reduced pressure. Water and ethyl acetate were added to the residue. The solid remaining undissolved was collected by filtration to give 7-O-tert-butyldimethylsilyl-1,7,11-trideacetylpyripyropene A (65 mg). The mother liquid was extracted with ethyl acetate. The ethyl acetate layer was then washed with saturated brine and was dried over anhydrous magnesium sulfate. The solvent was removed by evaporation under the reduced pressure to give 7-O-tert-butyldimethylsilyl-1,7,11-trideacetylpyripyropene A (235 mg). Thus, 300 mg in total (yield in two stages from Example 2: 95%) of 7-O-tert-butyldimethylsilyl-1,7,11-trideacetylpyripyropene A was obtained.

ESI-MS: m/z 572 (M+H)$^+$;
$^1$H-NMR (CD$_3$OD): δ 0.08 (3H, s), 0.13 (3H, s), 0.64 (3H, s), 0.90 (9H, s), 1.19 (1H, dt, J=3.6, 12.8 Hz), 1.31 (3H, s), 1.33-1.36 (2H, m), 1.48 (1H, t, J=12.0 Hz), 1.53 (3H, s), 1.62-1.80 (3H, m), 1.99-2.03 (1H, m), 3.16 (1H, d, J=10.8 Hz), 3.44 (1H, d, J=10.8 Hz), 3.56 (1H, dd, J=4.8, 11.6 Hz), 3.76 (1H, dd, J=5.2, 11.2 Hz), 4.86 (1H, d, J=3.2 Hz), 6.47 (1H, s), 7.47 (1H, ddd, J=0.8, 4.8, 8.0 Hz), 8.17 (1H, dt, J=2.0, 8.4 Hz), 8.55 (1H, dd, J=2.0, 4.8 Hz), 8.91 (1H, dd, J=0.8, 2.4 Hz).

Example 4

Synthesis of 7-O-tert-butyldimethylsilyl-1,11-O-dicyclopropanecarbonyl-1,7,11-trideacetylpyripyropene A 7-O-tert-butyldimethylsilyl-1,7,11-trideacetylpyripyropene A (57 mg) synthesized by the process described in Example 3 was dissolved in N,N-dimethylformamide (2 mL). Pyridine (0.5 mL) was added to the solution at 0° C., the mixture was stirred at that temperature for 30 min, and cyclopropanecarbonyl chloride (62 mg) was added thereto. The mixture was stirred at that temperature for 3 hr, and the reaction solution was then poured into water and was extracted with chloroform. The chloroform layer was washed with saturated brine and was dried over anhydrous sodium sulfate, and the solvent was then removed by evaporation under the reduced pressure to give a crude product (87 mg) of 7-O-tert-butyldimethylsilyl-1,11-O-dicyclopropanecarbonyl-1,7,11-trideacetylpyripyropene A. The crude product was purified by preparative thin-layer column chromatography (Merck silica gel 60F$_{254}$ 0.5 mm, chloroform:methanol=30:1) to give 7-O-tert-butyldimethylsilyl-1,11-O-dicyclopropanecarbonyl-1,7,11-trideacetylpyripyropene A (67 mg, yield 95%).

ESI-MS: m/z 708 (M+H)$^+$;
$^1$H-NMR (CDCl$_3$): δ 0.11 (3H, s), 0.15 (3H, s), 0.85-0.88 (4H, m), 0.91 (3H, s), 0.96 (9H, s), 0.92-1.01 (4H, m), 1.25-1.36 (1H, m), 1.42 (3H, s), 1.45-1.47 (1H, m), 1.53-1.65 (5H, m), 1.58 (3H, s), 1.80-1.93 (2H, m), 2.12-2.16 (1H, m), 2.81 (1H, d, J=2.0 Hz), 3.65 (1H, d, J=12.0 Hz), 3.70 (1H, m), 3.91 (1H, d, J=11.6 Hz), 4.81 (1H, dd, J=4.8, 11.6 Hz), 4.98 (1H, m), 6.36 (1H, s), 7.41 (1H, dd, J=4.8, 8.0 Hz), 8.10 (1H, dt, J=2.0, 8.4 Hz), 8.69 (1H, dd, J=1.6, 4.8 Hz), 9.00 (1H, d, J=2.0 Hz).

Example 5

Synthesis of 1,11-O-dicyclopropanecarbonyl-1,7,11-trideacetylpyripyropene A

7-O-tert-butyldimethylsilyl-1,11-O-dicyclopropanecarbonyl-1,7,11-trideacetylpyripyropene A (100 mg) synthesized by the process described in Example 4 was dissolved in tetrahydrofuran (1.5 mL). Pyridine (0.6 mL) and hydrogen fluoride/pyridine (0.9 mL) were added to the solution at 0° C. The mixture was stirred at that temperature for 4 days, an aqueous sodium hydrogen carbonate solution was then added thereto, and the mixture was extracted with chloroform. The chloroform layer was washed with saturated brine and was dried over anhydrous sodium sulfate. The solvent was then removed by evaporation under the reduced pressure to give a crude product (92 mg) of 1,11-O-dicyclopropanecarbonyl-1,7,11-trideacetylpyripyropene A. The crude product was purified by preparative thin-layer column chromatography (Merck silica gel 60F$_{254}$ 0.5 mm, chloroform:methanol=20:1) to give 1,11-O-dicyclopropanecarbonyl-1,7,11-trideacetylpyripyropene A (79 mg, yield 95%).

ESI-MS: m/z 594 (M+H)$^+$;
$^1$H-NMR (CDCl$_3$): δ 0.85-0.88 (4H, m), 0.92 (3H, s), 0.96-1.01 (4H, m), 1.35 (1H, dt, J=4.0, 12.6 Hz), 1.42 (3H, s), 1.45-1.50 (2H, m), 1.56-1.63 (3H, m), 1.66 (3H, s), 1.79-1.93 (3H, m), 2.14 (1H, m), 2.17 (1H, d, J=3.6 Hz), 2.85 (1H, d, J=2.0 Hz), 3.74 (1H, d, J=12.0 Hz), 3.78-3.82 (1H, m), 3.86 (1H, d, J=11.6 Hz), 4.82 (1H, dd, J=5.2, 11.6 Hz), 4.99 (1H, m), 6.52 (1H, s), 7.42 (1H, dd, J=4.8, 8.0 Hz), 8.11 (1H, dt, J=1.9, 8.1 Hz), 8.70 (1H, dd, J=1.6, 4.8 Hz), 9.00 (1H, d, J=2.0 Hz).

Example 6

Synthesis of 7-deacetyl-7-O-tetrahydropyranylpyripyropene A

7-Deacetylpyripyropene A (500 mg) produced by the process described in Example 1 was dissolved in dichloromethane (10 mL), and 3,4-dihydropyran (372 mg) and pyridinium p-toluenesulfonate (348 mg) were added to the solution. The mixture was stirred at room temperature for 73.5 hr. The reaction solution was then poured into water and was extracted with chloroform. The chloroform layer was washed with saturated brine and was dried over anhydrous magnesium sulfate. The solvent was then removed by evaporation under the reduced pressure to give a crude product (742 mg) of 7-deacetyl-7-O-tetrahydropyranylpyripyropene A. The results of measurement by ESI-MS and $^1$H-NMR showed that the compound was PR-44 described in Japanese Patent Application Laid-Open No. 259569/1996.

Example 7

Synthesis of 1,7,11-trideacetyl-7-O-tetrahydropyranylpyripyropene A

7-Deacetyl-7-O-tetrahydropyranylpyripyropene A (742 mg) produced in Example 6 was dissolved in a 66% aqueous methanol solution (9 mL). Potassium carbonate (511 mg) was added to the solution, and the mixture was stirred at room temperature for 4 hr. Water was added thereto, and the solid remaining undissolved was collected by filtration to give 1,7,11-trideacetyl-7-O-tetrahydropyranylpyripyropene A (453 mg, yield in two stages from Example 6: 90%).
ESI-MS: m/z 542 (M+H)$^+$.

Example 8

Synthesis of 1,11-O-dicyclopropanecarbonyl-1,7,11-trideacetyl-7-O-tetrahydropyranylpyripyropene A 1,7,11-Trideacetyl-7-O-tetrahydropyranylpyripyropene A (450 mg) synthesized by the process described in Example 7 was dissolved in N,N-dimethylformamide (6 mL). Pyridine (3 mL) was added to the solution at 0° C., and the mixture was stirred at that temperature for 10 min. Cyclopropanecarbonyl chloride (525 mg) was added thereto. The mixture was stirred at that temperature for one hr. The reaction solution was then poured into water and was extracted with chloroform. The chloroform layer was washed with saturated brine and was dried over anhydrous magnesium sulfate, and the solvent was then removed by evaporation under the reduced pressure to give a crude product (800 mg) of 1,11-O-dicyclopropanecarbonyl-1,7,11-trideacetyl-7-O-tetrahydropyranylpyripyropene A.
ESI-MS: m/z 678 (M+H)$^+$.

Example 9

Synthesis of 1,11-O-dicyclopropanecarbonyl-1,7,11-trideacetylpyripyropene A 1,11-O-dicyclopropanecarbonyl-1,7,11-trideacetyl-7-O-tetrahydropyranylpyripyropene A (800 mg) produced in Example 8 was dissolved in methanol (8 mL), and p-toluenesulfonic acid monohydrate (142 mg) was added to the solution at 0° C. The mixture was stirred at that temperature for 21.5 hr. An aqueous sodium hydrogen carbonate solution was then added thereto. Methanol was removed by evaporation under the reduced pressure, and the residue was extracted with ethyl acetate. The ethyl acetate layer was washed with saturated brine and was dried over anhydrous magnesium sulfate. The solvent was then removed by evaporation under the reduced pressure to give a crude product (570 mg) of 1,11-O-dicyclopropanecarbonyl-1,7,11-trideacetylpyripyropene A. The crude product was purified by chromatography on silica gel (Mega Bond Elut (Varian), acetone:hexane=3:5) to give 1,11-O-dicyclopropanecarbonyl-1,7,11-trideacetylpyripyropene A (346 mg, yield in two stages from Example 8: 70%). ESI-MS data and $^1$H-NMR data of the compound were in agreement with those in Example 5.

Example 10

Synthesis of 1,7,11-trideacetylpyripyropene A

Pyripyropene A (1 g) was dissolved in a 66% aqueous methanol solution (15 mL). Potassium carbonate (355 mg) was added to the solution, and the mixture was stirred at room temperature for 20 hr. The solvent was then removed by evaporation under the reduced pressure. Ethyl acetate and water were added thereto, and crystals remaining undissolved were collected by filtration to give 1,7,11-trideacetylpyripyropene A (737 mg, yield 94%). The results of measurement by ESI-MS and $^1$H-NMR showed that the compound was PR-3 described in Japanese Patent Application Laid-Open No. 259569/1996.

Example 11

Synthesis of 1,7,11-trideacetyl-1,11-O-isopropylidenepyripyropene A 1,7,11-Trideacetylpyripyropene A (200 mg) synthesized by the process described in Example 10 was dissolved in N,N-dimethylformamide (2 mL). Acetone dimethyl acetal (456 mg) and pyridinium p-toluenesulfonate (550 mg) were added to the solution. The mixture was stirred at room temperature for 25.5 hr. The reaction solution was then poured into water and was extracted with chloroform. The chloroform layer was washed with a saturated aqueous sodium hydrogen carbonate solution and saturated brine and was dried over anhydrous sodium sulfate. The solvent was then removed by evaporation under the reduced pressure to give a crude product of 1,7,11-trideacetyl-1,11-O-isopropylidenepyripyropene A. The crude product was purified by preparative thin-layer column chromatography (Merck silica gel 60F$_{254}$ 0.5 mm, chloroform:methanol=10:1) to give 1,7,11-trideacetyl-1,11-O-isopropylidenepyripyropene A (171 mg, yield 79%). The results of measurement by ESI-MS and $^1$H-NMR showed that the compound was PR-16 described in Japanese Patent Application Laid-Open No. 269065/1996.

Example 12

Synthesis of 7-O-tert-butyldimethylsilyl-1,7,11-trideacetyl-1,11-O-isopropylidenepyripyropene A 1,7,11-Trideacetyl-1,11-O-isopropylidenepyripyropene A (168 mg) synthesized by the process described in Example 11 was dissolved in N,N-dimethylformamide (2 mL). Imidazole (92 mg) and tert-butyldimethylchlorosilane (204 mg) were added to the solution. The mixture was stirred at room temperature for 22 hr, and the reaction solution was then poured into water and was extracted with chloroform. The chloroform layer was washed with saturated brine and was dried over anhydrous sodium sulfate. The solvent was then removed by evaporation under the reduced pressure to give a crude product (193 mg) of 7-O-tert-butyldimethylsilyl-1,7,11-trideacetyl-1,11-O-isopropylidenepyripyropene A. The crude product was purified by preparative thin-layer column chromatography (Merck silica gel 60F$_{254}$ 0.5 mm, chloroform:methanol=20:1) to give 7-O-tert-butyldimethylsilyl-1,7,11-trideacetyl-1,11-O-isopropylidenepyripyropene A (187 mg, yield 90%).

ESI-MS: m/z 612 (M+H)$^+$;

$^1$H-NMR (CDCl$_3$): δ 0.11 (3H, s), 0.16 (3H, s), 0.96 (9H, s), 1.03 (1H, m), 1.10 (3H, s), 1.33 (1H, dt, J=3.6, 12.8 Hz), 1.40 (3H, s), 1.43 (3H, s), 1.44 (3H, s), 1.39-1.44 (1H, m), 1.55-1.58 (2H, m), 1.58 (3H, s), 1.64 (1H, q, J=12.0 Hz), 1.81 (1H, dq, J=3.6, 12.8 Hz), 2.20 (1H, dt, J=3.2, 12.8 Hz), 2.81 (1H, d, J=1.6 Hz), 3.42 (1H, d, J=10.8 Hz), 3.51 (1H, d, J=10.4 Hz), 3.50-3.53 (1H, m), 3.72 (1H, dd, J=4.8, 11.2 Hz), 4.97 (1H, m), 6.35 (1H, s), 7.41 (1H, dd, J=4.8, 8.0 Hz), 8.10 (1H, dt, J=1.6, 8.0 Hz), 8.69 (1H, dd, J=1.6, 4.8 Hz), 9.00 (1H, d, J=2.0 Hz).

Example 13

Synthesis of 7-O-tert-butyldimethylsilyl-1,7,11-trideacetylpyripyropene A

7-O-tert-butyldimethylsilyl-1,7,11-trideacetyl-1,11-O-isopropylidenepyripyropene A (116 mg) synthesized by the process described in Example 12 was dissolved in tetrahydrofuran (1 mL), and 63% acetic acid (4 mL) was added to the solution at 0° C. The mixture was stirred at room temperature for 24 hr. An aqueous sodium hydrogen carbonate solution was added thereto, and the mixture was extracted with chloroform. The chloroform layer was washed with a saturated aqueous sodium hydrogen carbonate solution and saturated brine and was dried over anhydrous sodium sulfate. The solvent was then removed by evaporation under the reduced pressure to give a crude product (101 mg) of 7-O-tert-butyldimethylsilyl-1,7,11-trideacetylpyripyropene A. The crude product was purified by preparative thin-layer column chromatography (Merck silica gel 60F$_{254}$ 0.5 mm, chloroform:methanol=10:1) to give 7-O-tert-butyldimethylsilyl-1,7,11-trideacetylpyripyropene A (91 mg, yield 84%).

ESI-MS: m/z 572 (M+H)$^+$;

$^1$H-NMR (CD$_3$OD): δ 0.08 (3H, s), 0.13 (3H, s), 0.64 (3H, s), 0.90 (9H, s), 1.19 (1H, dt, J=3.6, 12.8 Hz), 1.31 (3H, s), 1.33-1.36 (2H, m), 1.48 (1H, t, J=12.0 Hz), 1.53 (3H, s), 1.62-1.80 (3H, m), 1.99-2.03 (1H, m), 3.16 (1H, d, J=10.8 Hz), 3.44 (1H, d, J=10.8 Hz), 3.56 (1H, dd, J=4.8, 11.6 Hz), 3.76 (1H, dd, J=5.2, 11.2 Hz), 4.86 (1H, d, J=3.2 Hz), 6.47 (1H, s), 7.47 (1H, ddd, J=0.8, 4.8, 8.0 Hz), 8.17 (1H, dt, J=2.0, 8.4 Hz), 8.55 (1H, dd, J=2.0, 4.8 Hz), 8.91 (1H, dd, J=0.8, 2.4 Hz).

Example 14

Synthesis of 1,11-dideacetyl-1,11-O-isopropylidenepyripyropene A 1,7,11-Trideacetyl-1,11-O-isopropylidenepyripyropene A (100 mg) synthesized by the process described in Example 11 was dissolved in dichloromethane (2 mL). Triethylamine (61 mg), 4-dimethylaminopyridine (7 mg), and acetic anhydride (26 mg) were added to the solution. The mixture was stirred at room temperature for 4 hr. The reaction solution was then poured into water and was extracted with chloroform. The chloroform layer was washed with saturated brine and was dried over anhydrous sodium sulfate, and the solvent was then removed by evaporation under the reduced pressure to give a crude product (120 mg) of 1,11-dideacetyl-1,11-O-isopropylidenepyripyropene A. The crude product was purified by preparative thin-layer column chromatography (Merck silica gel 60F$_{254}$ 0.5 mm, chloroform:methanol=20:1) to give 1,11-dideacetyl-1,11-O-isopropylidenepyripyropene A (103 mg, yield 95%). The results of measurement by ESI-MS and $^1$H-NMR showed that the compound was PR-43 described in Japanese Patent Application Laid-Open No. 269065/1996.

Example 15

Synthesis of 1,11-dideacetylpyripyropene A 1,11-Dideacetyl-1,11-O-isopropylidenepyripyropene A (99 mg) synthesized by the process described in Example 14 was dissolved in tetrahydrofuran (1.2 mL) and methanol (2.4 mL), and pyridinium p-toluenesulfonate (185 mg) was added to the solution. The mixture was stirred at room temperature for 30 hr, triethylamine was then added thereto, and the solvent was removed by evaporation under the reduced pressure. Chloroform and water were added to the residue, and the mixture was extracted with chloroform. The chloroform layer was washed with saturated brine and was dried over anhydrous sodium sulfate, and the solvent was removed by evaporation under the reduced pressure to give a crude product (85 mg) of 1,11-dideacetylpyripyropene A. The crude product was purified by preparative thin-layer column chromatography (Merck silica gel 60F$_{254}$ 0.5 mm, chloroform:methanol=60:1) to give 1,11-dideacetylpyripyropene A (64 mg, yield 72%). The results of measurement by ESI-MS and $^1$H-NMR showed that the compound was PR-5 described in Japanese Patent Application Laid-Open No. 259569/1996.

Example 15a

Synthesis of 1,11-dideacetylpyripyropene A 1,7,11-Trideacetylpyripyropene A (9.67 g) was suspended in N,N-dimethylformamide (48 mL). Acetone dimethyl acetal (6.61 g) and p-toluenesulfonic acid monohydrate (0.08 g) were added to the suspension, and the mixture was stirred at 38 to 41° C. for 4 hr. 4-Dimethylaminopyridine (0.08 g) was added thereto, and the mixture was removed by evaporation under the reduced pressure for 1.5 hr. The residue was cooled to 0° C. Triethylamine (2.57 g) and acetic anhydride (2.37 g) were added to the cooled solution, and the mixture was stirred at that temperature for 16 hr. Water (96 g) was then added to the reaction solution, and the mixture was adjusted to pH 7.17 by the addition of 5% hydrochloric acid. The precipitated light yellow powder was collected by filtration and was washed twice with water (20 g). The crude product thus obtained was suspended with methanol (48 mL), 15% hydrochloric acid (4.7 g) was added to the suspension, and the mixture was stirred at 25 to 27° C. for 2 hr. Water (33 mL) was added thereto, and the insolubles were filtered, followed by adjustment of pH to 4.41 by the addition of a 5% aqueous sodium hydroxide solution. Further, water (31 mL) was added thereto. The precipitated light yellow powder was collected by filtration and was washed twice with a 30% aqueous methanol solution (20 mL). The washed powder was dried at 40° C. for 23 hr to give 8.62 g of 1,11-dideacetylpyripyropene A. The results of measurement by $^1$H-NMR showed that the $^1$H-NMR data were in agreement with those of the compound produced in Example 15.

Example 16

Synthesis of 1,11-O-dicyclopropanecarbonyl-1,11-dideacetylpyripyropene A 1,11-Dideacetylpyripyropene A (61 mg) synthesized by the process described in Example 15 was dissolved in N,N-dimethylformamide (1.2 mL). Pyridine (0.3 mL) was added to the solution at 0° C., the mixture was stirred at that temperature for 10 min, cyclopropanecarbonyl chloride (77 mg) was added thereto, and the mixture was stirred at that temperature for 1.5 hr. The reaction solution was then poured into water and was extracted with chloroform. The chloroform layer was washed with saturated brine and was dried over anhydrous magnesium sulfate. The solvent was then removed by evaporation under the reduced pressure to give a crude product (97 mg) of 1,11-O-dicyclopropanecarbonyl-1,11-dideacetylpyripyropene A. The crude product was purified by preparative thin-layer column chromatography (Merck silica gel 60$F_{254}$ 0.5 mm, chloroform:methanol=20:1) to give 1,11-O-dicyclopropanecarbonyl-1,11-dideacetylpyripyropene A (73 mg, yield 93%).

ESI-MS: m/z 636 $(M+H)^+$;
$^1$H-NMR (CDCl$_3$): δ 0.84-0.89 (4H, m), 0.89 (3H, s), 0.90-1.06 (4H, m), 1.37 (1H, dt, J=3.8, 13.2 Hz), 1.45 (3H, s), 1.53 (1H, d, J=4.0 Hz), 1.55-1.67 (4H, m), 1.70 (3H, s), 1.79-1.87 (2H, m), 1.89-1.94 (2H, m), 2.14-2.18 (1H, m), 2.16 (3H, s), 2.97 (1H, d, J=2.0 Hz), 3.77 (2H, s), 4.81 (1H, dd, J=4.8, 11.7 Hz), 5.00 (1H, m), 5.02 (1H, dd, J=5.0, 11.4 Hz), 6.46 (1H, s), 7.40 (1H, dd, J=4.9, 8.0 Hz), 8.09 (1H, dt, J=1.9, 8.1 Hz), 8.68 (1H, dd, J=1.6, 4.8 Hz), 9.00 (1H, d, J=2.0 Hz).

Example 16a

Synthesis of 1,11-O-dicyclopropanecarbonyl-1,11-dideacetylpyripyropene A 1,11-Dideacetylpyripyropene A (25.76 g) was suspended in ethyl acetate (130 mL), pyridine (15.84 g) was added to the suspension. The mixture was cooled to 10 to 15° C. Cyclopropanecarbonyl chloride (15.70 g) was added dropwise thereto, and the mixture was stirred at 25 to 30° C. for 3 hr. The reaction solution was again cooled to 10 to 15° C., and water (50 mL) was added dropwise thereto. The mixture was adjusted to pH 2.59 by the addition of 5 N-hydrochloric acid, followed by separation. The organic layer was washed with 5% sodium bicarbonate water (50 mL) and 10% brine (50 mL) in that order. The ethyl acetate solution thus obtained was removed by evaporation under the reduced pressure and was further replaced with methanol to adjust the liquid volume to about 130 mL. Water (130 mL) was added dropwise thereto. The precipitated light yellow powder was collected by filtration, was washed twice with a 50% aqueous methanol solution (40 mL), and was dried at 40° C. for 23 hr to give 30.80 g of 1,11-O-dicyclopropanecarbonyl-1,11-dideacetylpyripyropene A. The results of measurement by $^1$H-NMR showed that the $^1$H-NMR data were in agreement with those of the compound produced in Example 16.

Example 17

Synthesis of 1,11-O-dicyclopropanecarbonyl-1,7,11-trideacetylpyripyropene A 1,11-O-dicyclopropanecarbonyl-1,11-dideacetylpyripyropene A (67 mg) synthesized by the process described in Example 16 was dissolved in a 95% aqueous methanol solution (0.07 mL). Sodium carbonate (22 mg) was added to the solution at 0° C. The mixture was stirred at that temperature for 4 days. Acetic acid was then added thereto. Methanol was removed by evaporation under the reduced pressure, and the residue was extracted with chloroform. The chloroform layer was washed with saturated brine and was dried over anhydrous sodium sulfate. The solvent was then removed by evaporation under the reduced pressure to give a crude product (74 mg) of 1,11-O-dicyclopropanecarbonyl-1,7,11-trideacetylpyripyropene A. The crude product was purified by preparative thin-layer column chromatography (Merck silica gel 60$F_{254}$ 0.5 mm, chloroform:methanol=10:1) to give 1,11-O-dicyclopropanecarbonyl-1,7,11-trideacetylpyripyropene A (47 mg, yield 76%). ESI-MS data and $^1$H-NMR data of the compound were in agreement with those of the compound produced in Example 5.

Example 17a

Synthesis of 1,11-O-dicyclopropanecarbonyl-1,7,11-trideacetylpyripyropene A 1,11-O-dicyclopropanecarbonyl-1,11-dideacetylpyripyropene A (30.00 g) was suspended in a mixed liquid composed of water (20 mL) and methanol (190 mL), and the mixture was cooled to 0 to 5° C. A 1 M methanol solution (4.49 mL) of sodium methoxide was added thereto, and the mixture was stirred at that temperature for 23 hr. 1.2% hydrochloric acid (20 mL) was added to the reaction solution, and the mixture was filtered through a 0.5-μm filter, followed by evaporation under the reduced pressure to adjust the liquid volume to about 90 mL. A mixed liquid (120 mL) of methanol/water=2/1 was added to the residue to adjust the liquid volume to about 150 mL. Further, a mixed liquid (120 mL) of methanol/water=2/1 was added thereto to adjust the liquid volume to about 180 mL. The mixture was stirred at room temperature for one hr, was then cooled to 5° C., and was stirred for 17 hr. The precipitated light yellow powder was collected by filtration, was washed twice with a 30% aqueous methanol solution (50 mL), and was dried at 40° C. for 22 hr to give 23.82 g of 1,11-O-dicyclopropanecarbonyl-1,7,11-trideacetylpyripyropene A. The results of measurement by $^1$H-NMR showed that the $^1$H-NMR data were in agreement with those of the compound produced in Example 17.

Example 18

Synthesis of 7-O-chloroacetyl-1,7,11-trideacetyl-1,11-O-isopropylidenepyripyropene A 1,7,11-Trideacetyl-1,11-O-isopropylidenepyripyropene A (100 mg) synthesized by the process described in Example 11 was dissolved in tetrahydrofuran (2 mL), and triethylamine (61 mg) and chloroacetic anhydride (103 mg) were added to the solution. The mixture was stirred at room temperature for 3.5 hr, and the reaction solution was then poured into water and was extracted with chloroform. The chloroform layer was washed with saturated brine and was dried over anhydrous sodium sulfate. The solvent was then removed by evaporation under the reduced pressure to give a crude product (118 mg) of 7-O-chloroacetyl-1,7,11-trideacetyl-1,11-O-isopropylidenepyripyropene A. The crude product was purified by preparative thin-layer column chromatography (Merck silica gel 60$F_{254}$ 0.5 mm, chloroform:methanol=20:1) to give 7-O-chloroacetyl-1,7,11-trideacetyl-1,11-O-isopropylidenepyripyropene A (80 mg, yield 70%).

ESI-MS: m/z 574 $(M+H)^+$;
$^1$H-NMR (CDCl$_3$): δ 1.11 (3H, s), 1.16 (1H, dd, J=2.4, 12.6 Hz), 1.33-1.41 (1H, m), 1.44 (3H, s), 1.45 (3H, s), 1.52 (1H, d, J=4.0 Hz), 1.58-1.65 (1H, m), 1.62 (3H, s), 1.70 (3H, s), 1.66-1.75 (2H, m), 1.77-1.86 (1H, m), 2.22 (1H, m), 2.90 (1H, d, J=2.0 Hz), 3.48 (2H, s), 3.54 (1H, dd, J=3.6, 12.0 Hz), 4.19 (2H, d, J=4.0 Hz), 5.00 (1H, m), 5.09 (1H, dd, J=5.6, 11.6 Hz), 6.45 (1H, s), 7.41 (1H, dd, J=4.8, 8.0 Hz), 8.10 (1H, dt, J=1.6, 8.0 Hz), 8.70 (1H, dd, J=1.6, 4.8 Hz), 9.02 (1H, d, J=1.6 Hz).

Example 19

Synthesis of 7-O-chloroacetyl-1,7,11-trideacetylpyripyropene A

7-O-chloroacetyl-1,7,11-trideacetyl-1,11-O-isopropylidenepyripyropene A (35 mg) synthesized by the process described in Example 18 was dissolved in tetrahydrofuran (0.6 mL) and methanol (1.2 mL), and pyridinium p-toluenesulfonate (61 mg) was added to the solution. The mixture was stirred at room temperature for 31 hr, and the reaction solution was then poured into water and was extracted with chloroform. The chloroform layer was washed with saturated brine and was dried over anhydrous sodium sulfate. The solvent was then removed by evaporation under the reduced pressure to give a crude product (30 mg) of 7-O-chloroacetyl-1,7,11-trideacetylpyripyropene A. The crude product was purified by preparative thin-layer column chromatography (Merck silica gel 60$F_{254}$ 0.5 mm, chloroform:methanol=10:1) to give 7-O-chloroacetyl-1,7,11-trideacetylpyripyropene A (24 mg, yield 74%).
ESI-MS: m/z 534 (M+H)$^+$;
$^1$H-NMR (CD$_3$OD): δ 0.74 (3H, s), 1.32 (1H, m), 1.44 (3H, s), 1.54 (2H, m), 1.69-1.75 (2H, m), 1.75 (3H, s), 1.79-1.86 (1H, m), 1.91-1.94 (1H, m), 2.12 (1H, m), 3.26 (1H, d, J=11.6 Hz), 3.52 (1H, d, J=10.8 Hz), 3.67 (1H, dd, J=5.2, 11.6 Hz), 4.33 (2H, d, J=2.4 Hz), 4.98 (1H, m), 5.15 (1H, dd, J=5.2, 11.6 Hz), 6.79 (1H, s), 7.55 (1H, dd, J=4.8, 8.0 Hz), 8.28 (1H, dt, J=2.4, 8.0 Hz), 8.62 (1H, dd, J=1.6, 4.8 Hz), 9.02 (1H, d, J=2.4 Hz).

Example 20

Synthesis of 7-O-chloroacetyl-1,11-O-dicyclopropanecarbonyl-1,7,11-trideacetylpyripyropene A 7-O-chloroacetyl-1,7,11-trideacetylpyripyropene A (21 mg) synthesized by the process described in Example 19 was dissolved in N,N-dimethylformamide (1.2 mL), and pyridine (0.3 mL) and cyclopropanecarbonyl chloride (25 mg) were added to the solution at 0° C. The mixture was stirred at that temperature for 2.5 hr. The reaction solution was then poured into water, and the mixture was extracted with chloroform. The chloroform layer was washed with saturated brine and was dried over anhydrous magnesium sulfate. The solvent was then removed by evaporation under the reduced pressure to give a crude product (37 mg) of 7-O-chloroacetyl-1,11-O-dicyclopropanecarbonyl-1,7,11-trideacetylpyripyropene A. The crude product was purified by preparative thin-layer column chromatography (Merck silica gel 60$F_{254}$ 0.5 mm, chloroform:methanol=30:1) to give 7-O-chloroacetyl-1,11-O-dicyclopropanecarbonyl-1,7,11-trideacetylpyripyropene A (16 mg, yield 58%).
ESI-MS: m/z 670 (M+H)$^+$;
$^1$H-NMR (CDCl$_3$): δ 0.85-0.90 (4H, m), 0.91 (3H, s), 0.96-1.08 (4H, m), 1.38 (1H, dt, J=4.0, 12.6 Hz), 1.45 (3H, s), 1.54-1.67 (5H, m), 1.72 (3H, s), 1.81-1.95 (3H, m), 2.17 (1H, m), 2.89 (1H, d, J=1.6 Hz), 3.78 (2H, s), 4.17 (2H, d, J=2.8 Hz), 4.82 (1H, dd, J=4.8, 11.6 Hz), 5.01 (1H, m), 5.09 (1H, dd, J=5.2, 11.6 Hz), 6.45 (1H, s), 7.41 (1H, dd, J=4.8, 8.0 Hz), 8.10 (1H, dt, J=1.6, 8.0 Hz), 8.69 (1H, dd, J=1.6, 4.8 Hz), 9.02 (1H, d, J=1.6 Hz).

Example 21

Synthesis of 1,11-O-dicyclopropanecarbonyl-1,7,11-trideacetylpyripyropene A

7-O-chloroacetyl-1,11-O-dicyclopropanecarbonyl-1,7,11-trideacetylpyripyropene A (14 mg) synthesized by the process described in Example 20 was dissolved in a 95% aqueous methanol solution (1.4 mL). Sodium hydrogen carbonate (1.9 mg) was then added to the solution. The mixture was stirred at room temperature for 3 hr. Acetic acid was added thereto, and methanol was then removed by evaporation under the reduced pressure to give a crude product of 1,11-O-dicyclopropanecarbonyl-1,7,11-trideacetylpyripyropene A. The crude product was purified by preparative thin-layer column chromatography (Merck silica gel 60$F_{254}$ 0.5 mm, chloroform:methanol=10:1) to give 1,11-O-dicyclopropanecarbonyl-1,7,11-trideacetylpyripyropene A (12 mg, yield 94%). ESI-MS data and $^1$H-NMR data of the compound were in agreement with those of the compound produced in Example 5.

Example 22

Synthesis of 1,11-O-benzylidene-1,7,11-trideacetylpyripyropene A 1,7,11-Trideacetylpyripyropene A (1.0 g) synthesized by the process described in Example 10 was dissolved in N,N-dimethylformamide (10 mL). Pyridinium p-toluenesulfonate (2.75 g) and benzaldehyde dimethyl acetal (3.3 g) were added to the solution. The mixture was stirred at room temperature for 5 hr. The reaction solution was then poured into water, and the mixture was extracted with ethyl acetate. The ethyl acetate layer was washed with saturated brine and was dried over anhydrous sodium sulfate, and the solvent was then removed by evaporation under the reduced pressure to give a crude product of 1,11-O-benzylidene-1,7,11-trideacetylpyripyropene A. The crude product was purified by chromatography on silica gel (Mega Bond Elut (Varian), acetone:chloroform=1:10) to give 1,11-O-benzylidene-1,7,11-trideacetylpyripyropene A (887 mg, yield 74%). The results of measurement by ESI-MS and $^1$H-NMR showed that the compound was PR-93 described in Japanese Patent Application Laid-Open No. 269065/1996.

Example 23

Synthesis of 1,11-O-benzylidene-7-O-chloroacetyl-1,7,11-trideacetylpyripyropene A 1,11-O-benzylidene-1,7,11-trideacetylpyripyropene A (1.0 g) synthesized by the process described in Example 22 was dissolved in pyridine (2.5 mL). Chloroacetic anhydride (206 mg) was added to the solution at 0° C. The mixture was stirred at that temperature for 1.5 hr, and the reaction solution was then poured into water. The mixture was extracted with ethyl acetate. The ethyl acetate layer was washed with saturated brine and was dried over anhydrous sodium sulfate. The solvent was then removed by evaporation under the reduced pressure to give a crude product of 1,11-O-benzylidene-7-O-chloroacetyl-1,7,11-trideacetylpyripyropene A. The crude product was purified by chromatography on silica gel (Mega Bond Elut (Varian), acetone:hexane=1:100) to give 1,11-O-benzylidene-7-O-chloroacetyl-1,7,11-trideacetylpyripyropene A (359 mg, yield 72%).
ESI-MS: m/z 622 (M+H)$^+$;
$^1$H-NMR (CDCl$_3$): δ 1.19-1.22 (1H, m), 1.25 (3H, s), 1.41 (1H, m), 1.48 (3H, s), 1.53-1.56 (1H, m), 1.70 (3H, s), 1.70-1.84 (3H, m), 1.95 (1H, m), 2.27 (1H, m), 2.88 (1H, d, J=1.6 Hz), 3.49 (1H, d, J=10.4 Hz), 3.50-3.53 (1H, m), 3.89 (1H, d, J=10.4 Hz), 4.20 (2H, d, J=3.2 Hz), 5.02 (1H, m), 5.12 (1H, dd, J=5.2, 11.6 Hz), 5.54 (1H, s), 6.46 (1H, s), 7.33-7.43 (4H, m), 7.51 (2H, dd, J=1.6, 8.0 Hz), 8.11 (1H, dt, J=2.0, 8.0 Hz), 8.70 (1H, dd, J=1.6, 4.8 Hz), 9.02 (1H, d, J=2.0 Hz).

Example 24

Synthesis of 7-O-chloroacetyl-1,7,11-trideacetylpyripyropene A 1,11-O-benzylidene-7-O-chloroacetyl-1,7,11-trideacetylpyripyropene A (10 mg) synthesized by the process described in Example 23 was dissolved in chloroform (1 mL) and methanol (9 mL), and 10-camphorsulfonic acid (3 mg) was added to the solution. The mixture was stirred at room temperature for 5 days. The reaction solution was then poured into water, and the mixture was extracted with chloroform. The chloroform layer was washed with saturated brine and was dried over anhydrous sodium sulfate. The solvent was then removed by evaporation under the reduced pressure to give a crude product of 7-O-chloroacetyl-1,7,11-trideacetylpyripyropene A. The crude product was purified by chromatography on silica gel (Mega Bond Elut (Varian), acetone:chloroform=1:10) to give 7-O-chloroacetyl-1,7,11-trideacetylpyripyropene A (8 mg, yield 100%). ESI-MS data and $^1$H-NMR data of the compound were in agreement with those of the compound produced in Example 19.

Example 25

Synthesis of 1,7,11-trideacetyl-1,11-O-p-methoxybenzylidenepyripyropene A 1,7,11-Trideacetylpyripyropene A (1.0 g) synthesized by the process described in Example 10 was dissolved in N,N-dimethylformamide (22 mL). Pyridinium p-toluenesulfonate (2.76 g) and p-methoxybenzaldehyde dimethyl acetal (0.4 g) were added to the solution. The mixture was stirred at room temperature for 4 hr. The reaction solution was then poured into water, and the mixture was extracted with ethyl acetate. The ethyl acetate layer was washed with saturated brine and was dried over anhydrous sodium sulfate. The solvent was removed by evaporation under the reduced pressure to give a crude product of 1,7,11-trideacetyl-1,11-O-p-methoxybenzylidenepyripyropene A. The crude product was purified by chromatography on silica gel (Mega Bond Elut (Varian), acetone:chloroform=1:10) to give 1,7,11-trideacetyl-1,11-O-p-methoxybenzylidenepyripyropene A (520 mg, yield 41%). The results of measurement by ESI-MS and $^1$H-NMR showed that the compound was PR-124 described in Japanese Patent Application Laid-Open No. 269065/1996.

Example 26

Synthesis of 7-O-chloroacetyl-1,7,11-trideacetyl-1,11-O-p-methoxybenzylidenepyripyropene A 1,7,11-Trideacetyl-1,11-O-p-methoxybenzylidene-pyripyropene A (100 mg) synthesized by the process described in Example 25 was dissolved in tetrahydrofuran (2 mL). Triethylamine (50 mg) and chloroacetic anhydride (60 mg) were added to the solution. The mixture was stirred at room temperature for 2.5 hr, and the reaction solution was then poured into water and was extracted with chloroform. The chloroform layer was washed with saturated brine and was dried over anhydrous sodium sulfate. The solvent was then removed by evaporation under the reduced pressure to give a crude product of 7-O-chloroacetyl-1,7,11-trideacetyl-1,11-O-p-methoxybenzylidene-pyripyropene A. The crude product was recrystallized from methanol and ethyl acetate, and the recrystallized product was further purified by chromatography on silica gel (Mega Bond Elut (Varian), acetone:chloroform=1:30) to give 7-O-chloroacetyl-1,7,11-trideacetyl-1,11-O-p-methoxybenzylidenepyripyropene A (83 mg, yield 75%).

ESI-MS: m/z 652 (M+H)$^+$;

$^1$H-NMR (CDCl$_3$): δ 1.20 (1H, m), 1.24 (3H, s), 1.40 (1H, m), 1.47 (3H, s), 1.54 (1H, d, J=3.6 Hz), 1.72 (3H, s), 1.66-1.80 (3H, m), 1.93 (1H, m), 2.26 (1H, m), 2.87 (1H, d, J=2.0 Hz), 3.47 (1H, d, J=10.0 Hz), 3.47-3.51 (1H, m), 3.80 (3H, s), 3.87 (1H, d, J=10.4 Hz), 4.20 (2H, d, J=3.2 Hz), 5.01 (1H, m), 5.12 (1H, dd, J=5.6, 11.6 Hz), 5.50 (1H, s), 6.46 (1H, s), 6.90 (2H, d, J=8.8 Hz), 7.41 (1H, dd, J=4.8, 12.0 Hz), 7.43 (2H, d, J=8.8 Hz), 8.10 (1H, dt, J=2.0, 8.4 Hz), 8.70 (1H, dd, J=2.4, 4.8 Hz), 9.02 (1H, d, J=2.0 Hz).

Example 27

Synthesis of 7-O-chloroacetyl-1,7,11-trideacetylpyripyropene A

7-O-chloroacetyl-1,7,11-trideacetyl-1,11-O-p-methoxybenzylidenepyripyropene A (30 mg) synthesized by the process described in Example 26 was dissolved in chloroform (5 mL) and methanol (1 mL), and 10-camphorsulfonic acid (3 mg) was added to the solution. The mixture was stirred at room temperature for 5 days, and the reaction solution was then poured into water and was extracted with chloroform. The chloroform layer was washed with saturated brine and was dried over anhydrous sodium sulfate. The solvent was then removed by evaporation under the reduced pressure to give a crude product of 7-O-chloroacetyl-1,7,11-trideacetylpyripyropene A. The crude product was purified by chromatography on silica gel (Mega Bond Elut (Varian), acetone:chloroform=1:5) to give 7-O-chloroacetyl-1,7,11-trideacetylpyripyropene A (14 mg, yield 69%). ESI-MS data and $^1$H-NMR data of the compound were in agreement with those of the compound produced in Example 19.

The invention claimed is:

1. A process for producing compound C represented by formula C:

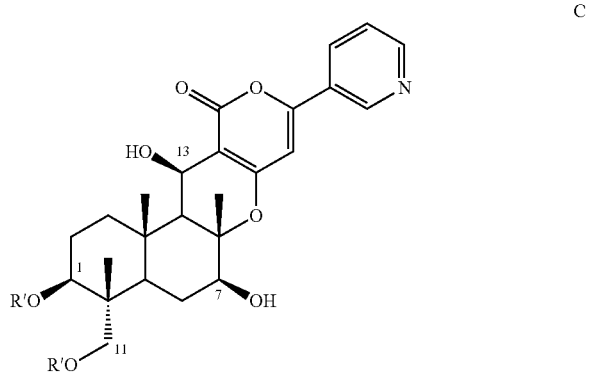

wherein R' represents cyclic $C_{3-6}$ alkylcarbonyl, the process comprising:
acylating hydroxyl at the 1- and 11-positions of compound Fb represented by formula Fb:

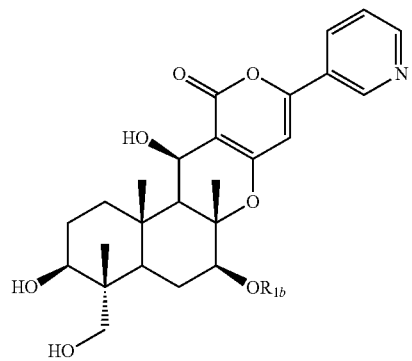

Fb wherein
$R_{1b}$ represents formyl; optionally substituted straight chain $C_{1-4}$ alkylcarbonyl;
optionally substituted benzyl; group —$SiR_3R_4R_5$ optionally substituted by halogen atom wherein $R_3$, $R_4$, and $R_5$ each independently represent straight chain or branched chain $C_{1-6}$ alkyl or phenyl; $C_{1-6}$ alkyloxy-$C_{1-6}$ alkyl optionally substituted by halogen atom; $C_{1-6}$ alkylthio-$C_{1-6}$ alkyl optionally substituted by halogen atom; straight chain, branched chain, or cyclic $C_{1-4}$ alkyl optionally substituted by halogen atom, provided that, when alkyl in the $C_{1-4}$ alkyl group is of a branched chain or cyclic type, the alkyl group is $C_{3-4}$ alkyl; $C_{2-6}$ alkenyl optionally substituted by halogen atom; $C_{2-6}$ alkynyl optionally substituted by halogen atom; or an optionally substituted saturated or unsaturated five- or six-membered heterocyclic group,
wherein, in $R_{1b}$, the substituent optionally possessed by alkylcarbonyl is selected from the group consisting of halogen atoms, $C_{1-4}$ alkyloxy, $C_{1-4}$ haloalkyloxy, $C_{1-4}$ alkylcarbonyl, $C_{1-4}$ haloalkylcarbonyl, $C_{1-4}$ alkylcarbonyloxy, and $C_{1-4}$ haloalkylcarbonyloxy, and the substituent optionally possessed by the heterocyclic group and benzyl is selected from the group consisting of halogen atoms, $C_{1-4}$ alkyl, $C_{1-4}$ alkyloxy, $C_{1-4}$ haloalkyloxy, $C_{1-4}$ alkylthio, $C_{1-4}$ haloalkyl, $C_{1-4}$ alkylcarbonyl, $C_{1-4}$ haloalkylcarbonyl, $C_{1-4}$ alkylcarbonyloxy, $C_{1-4}$ haloalkylcarbonyloxy, nitro, and cyano,
with an acylating agent corresponding to R' as defined above to give compound B2b represented by formula B2b:

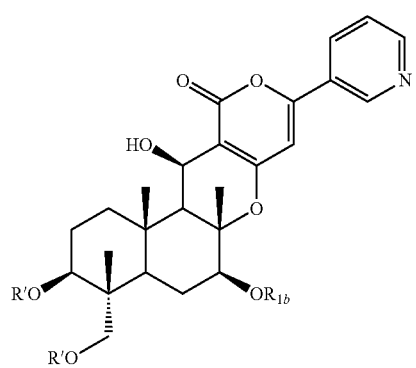

B2b wherein $R_{1b}$ and R' are as defined above,
and then removing $R_{1b}$ of compound B2b to produce compound C.

2. The process according to claim 1, further comprising, before acylation of hydroxyl at the 1- and 11-positions of compound Fb, the steps of:
hydrolyzing acyl at the 1-, 7-, and 11-positions of compound A4 represented by formula A4:

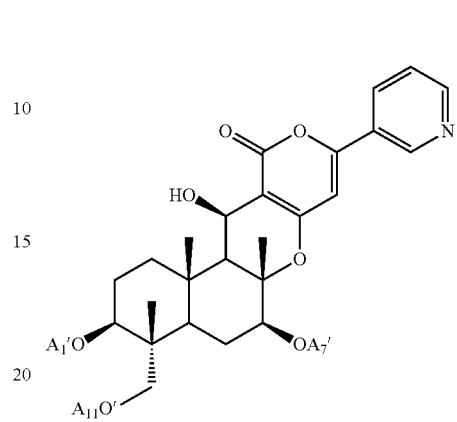

A4 wherein $A_1$, $A_7$, and $A_{11}$, which may be the same or different, represent acetyl or propionyl,
with a base to deacylate compound A4, then protecting hydroxyl at the 1- and 11-positions to give compound D represented by formula D:

[Chemical formula 6]

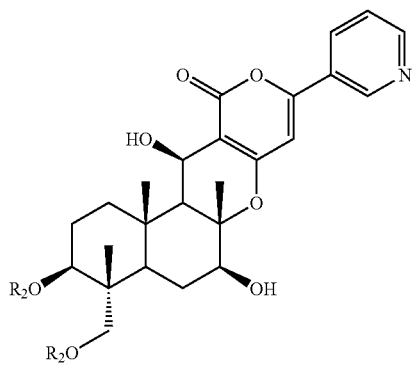

D wherein two $R_2$s together represent a group selected from groups represented by formulae D-1, D-2, D-3, and D-4:

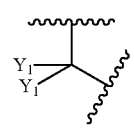

D-1

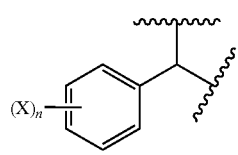

D-2

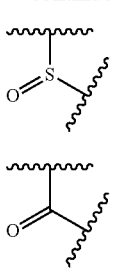

wherein $Y_1$ represents a hydrogen atom or $C_{1-4}$ alkyl; Xs, which may be the same or different, represent a hydrogen atom, $C_{1-4}$ alkoxy, or nitro; and n is 0 to 5, then protecting hydroxyl at the 7-position of compound D to give compound E represented by formula E:

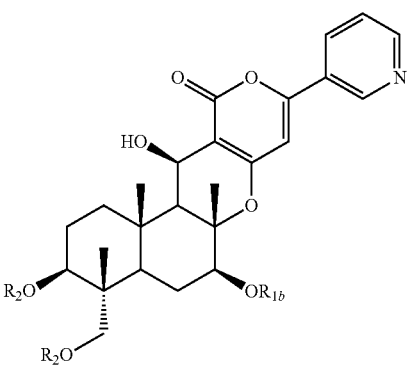

wherein $R_{1b}$ represents formyl; optionally substituted straight chain $C_{1-4}$ alkylcarbonyl; optionally substituted benzyl; group -SiR$_3$R$_4$R$_5$ optionally substituted by halogen atom wherein $R_3$, $R_4$, and $R_5$ each independently represent straight chain or branched chain $C_{1-6}$ alkyl or phenyl; $C_{1-6}$ alkyloxy-$C_{1-6}$ alkyl optionally substituted by halogen atom; $C_{1-6}$ alkylthio-$C_{1-6}$ alkyl optionally substituted by halogen atom; straight chain, branched chain, or cyclic $C_{1-4}$ alkyl optionally substituted by halogen atom, provided that, when alkyl in the $C_{1-4}$ alkyl group is of a branched chain or cyclic type, the alkyl group is $C_{3-4}$ alkyl; $C_{2-6}$ alkenyl optionally substituted by halogen atom; $C_{2-6}$ alkynyl optionally substituted by halogen atom; or an optionally substituted saturated or unsaturated five- or six-membered heterocyclic group, wherein, in $R_{1b}$, the substitutent optionally possessed by alkylcarbonyl is selected from the group consisting of halogen atoms, $C_{1-4}$ alkyloxy, $C_{1-4}$ haloalkyloxy, $C_{1-4}$ alkylcarbonyl, $C_{1-4}$ haloalkylcarbonyl, $C_{1-4}$ alkylcarbonyloxy, and $C_{1-4}$ haloalkylcarbonyloxy, and the substituent optionally possessed by the heterocyclic group and benzyl is selected from the group consisting of halogen atoms, $C_{1-4}$ alkyl, $C_{1-4}$ alkyloxy, $C_{1-4}$ haloalkyloxy, $C_{1-4}$ alkylthio, $C_{1-4}$ haloalkyl, $C_{1-4}$ alkylcarbonyl, $C_{1-4}$ haloalkylcarbonyl, $C_{1-4}$ alkylcarbonyloxy, $C_{1-4}$ haloalkylcarbonyloxy, nitro, and cyano, and $R_2$ is as defined above, and further removing the protective groups at the 1- and 11-positions of compound E to give compound Fb represented by formula Fb:

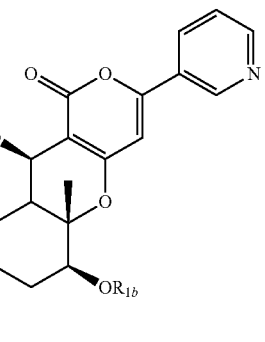

wherein $R_{1b}$ is as defined above.

3. The process according to claim 2, wherein $R_{1b}$ represents acetyl; chloroacetyl; or group —SiR$_3$R$_4$R$_5$ optionally substituted by halogen atom wherein $R_3$, $R_4$, and $R_5$ each independently represent straight chain or branched chain $C_{1-6}$ alkyl or phenyl, and wherein two $R_2$S together represent a group represented by formula D-1 or D-2:

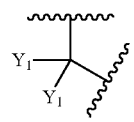

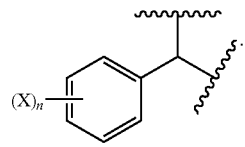

wherein $Y_1$ represents a hydrogen atom or $C_{1-4}$ alkyl; Xs, which may be the same or different, represent a hydrogen atom, $C_{1-4}$ alkoxy, or nitro; and n is 0 to 5.

* * * * *